US009132165B2

(12) United States Patent
Mahlapuu et al.

(10) Patent No.: US 9,132,165 B2
(45) Date of Patent: Sep. 15, 2015

(54) SYNTHETIC PEPTIDES AND THEIR USE

(75) Inventors: Margit Mahlapuu, Göteborg (SE);
Camilla Björn, Västra Frölunda (SE);
Veronika Sjöstrand, Göteborg (SE);
Björn Walse, Uppsala (SE); Bo Svenson, Södra Sandby (SE)

(73) Assignee: Pergamum AB, Solna (SE)

( * ) Notice: Subject to any disclaimer, the term of this patent is extended or adjusted under 35 U.S.C. 154(b) by 0 days.

(21) Appl. No.: 13/981,609

(22) PCT Filed: Jan. 25, 2012

(86) PCT No.: PCT/EP2012/051111
§ 371 (c)(1),
(2), (4) Date: Oct. 15, 2013

(87) PCT Pub. No.: WO2012/101156
PCT Pub. Date: Aug. 2, 2012

(65) Prior Publication Data
US 2014/0031296 A1    Jan. 30, 2014

(51) Int. Cl.
*A61K 38/10*   (2006.01)
*C07K 7/08*    (2006.01)
*C07K 14/79*   (2006.01)
*A23L 1/305*   (2006.01)
*A61K 38/40*   (2006.01)

(52) U.S. Cl.
CPC ............... *A61K 38/10* (2013.01); *A23L 1/3053* (2013.01); *C07K 7/08* (2013.01); *C07K 14/79* (2013.01); *A61K 38/40* (2013.01)

(58) Field of Classification Search
CPC ...... A23L 1/3053; A61K 38/10; A61K 38/40; C07K 14/79; C07K 7/08
See application file for complete search history.

(56) References Cited

U.S. PATENT DOCUMENTS

| 5,304,633 | A |   | 4/1994 | Tomita et al. |         |
|-----------|---|---|--------|---------------|---------|
| 5,595,756 | A | * | 1/1997 | Bally et al.  | 424/450 |

FOREIGN PATENT DOCUMENTS

| EP | 0 629 347      | 12/1994 |
| EP | 1 151 009      | 11/2001 |
| EP | 1 228 097      | 8/2002  |
| EP | 2 060 586      | 5/2009  |
| JP | 7-145196       | 6/1995  |
| JP | 7-274970       | 10/1995 |
| JP | 8-40925        | 2/1996  |
| JP | 8-143468       | 6/1996  |
| WO | WO 98/06425    | 2/1998  |
| WO | WO 00/01730    | 1/2000  |
| WO | WO 00/49040    | 8/2000  |
| WO | WO 02/100387   | 12/2002 |
| WO | WO 2006/047744 | 5/2006  |
| WO | WO 2008/096814 | 8/2008  |
| WO | WO 2008/096816 | 8/2008  |
| WO | WO 2009/050279 | 4/2009  |
| WO | WO 2009/062898 | 5/2009  |
| WO | WO 2010/081800 | 7/2010  |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Laura C. Moriarty, Factors contributing to the potency of antimicrobial cationic peptides from the N-terminal region of human lactoferrin, FEMS Microbiology Letters 239 (2004) 295-299.*
Carlo P.J.M. Brouwer, The Pharmacology of Radiolabeled Cationic Antimicrobial Peptides, Journal of Pharmaceutical Sciences, Vol. 97, No. 5, May 2008, pp. 1633-1651.*
Antonella Lupetti, Human Lactoferrin-Derived Peptide's Antifungal Activities against Disseminated *Candida albicans*, JID 2007:196 (Nov. 1), pp. 1416-1424. Infection.*
Orla M. Conneely, Antiinflammatory Activities of Lactoferrin, Journal of the American College of Nutrition, vol. 20, No. 5, pp. 389S-395S, 2001.*
Michael B. Sporn, Chemoprevention of Cancer, Carcinogenesis, vol. 21, No. 3, pp. 525-530, 2000.*
International Search Report issued in International Application No. PCT/EP2012/051112 and mailed on Apr. 11, 2013.
Haversen et al., *Structure-Microbicidal Activity Relationship of Synthetic Fragments Derived from the Antibacterial α-Helix of Human Lactoferrin*, 54(1) Antimicrobial Agents and Chemotherapy 418-425 (Jan. 2010).
Odell et al., *Antibacterial Activity of Peptides Homologous to a Loop Region in Human Lactoferrin*, 382(1) FEBS Letters 175-178 (Jan. 1, 1996).
Bellamy et al., *Antibacterial spectrum of lactoferricin B, a potent bactericidal peptide derived from the N-terminal region of bovine lactoferrin*, 73 Journal of Applied Bacteriology 472-479 (1992).
Bellamy et al., *Identification of the bactericidal domain of lactoferrin*, 1121 Biochimica et Biophysica Acta 130-136 (1992).

* cited by examiner

*Primary Examiner* — James H Alstrum Acevedo
*Assistant Examiner* — Erinne Dabkowski
(74) *Attorney, Agent, or Firm* — Buchanan Ingersoll & Rooney PC

(57) ABSTRACT

The present invention relates to new peptides and to use thereof, in particular for treatment and/or prevention of infections, inflammations, pain, wounds, scar and/or tumors.

12 Claims, 5 Drawing Sheets

```
SEQUENCE LISTING

<160> NUMBER OF SEQ ID NOS: 97

<210> SEQ ID NO 1
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: a fragment of human lactoferrin corresponding
      to amino acids 13-30

<400> SEQUENCE: 1

Gln Pro Glu Ala Thr Lys Cys Phe Gln Trp Gln Arg Asn Met Arg Lys
1               5                   10                  15

Val Arg

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Cys, Leu, Trp, Lys, Arg
<220> FEATURE:
<221> NAME/KEY: MISC_FEATURE
<222> LOCATION: (2)..(2)
<223> OTHER INFORMATION: Xaa can be Cys, Phe, Lys, Trp, Arg
<220> FEATURE:
<221> NAME/KEY: MISC_FEATURE
<222> LOCATION: (3)..(3)
<223> OTHER INFORMATION: Xaa can be Leu, Arg
<220> FEATURE:
<221> NAME/KEY: MISC_FEATURE
<222> LOCATION: (5)..(5)
<223> OTHER INFORMATION: Xaa can be Leu, Lys, Arg
<220> FEATURE:
<221> NAME/KEY: MISC_FEATURE
<222> LOCATION: (7)..(7)
<223> OTHER INFORMATION: Xaa can be Asn, Ser, Ala, Leu, Trp, Lys, Arg
<220> FEATURE:
<221> NAME/KEY: MISC_FEATURE
<222> LOCATION: (8)..(8)
<223> OTHER INFORMATION: Xaa can be Met, Trp, Ser
<220> FEATURE:
<221> NAME/KEY: MISC_FEATURE
```

```
<222> LOCATION: (9)..(9)
<223> OTHER INFORMATION: Xaa can be Arg, Val
<220> FEATURE:
<221> NAME/KEY: MISC_FEATURE
<222> LOCATION: (11)..(11)
<223> OTHER INFORMATION: Xaa can be Val, Ala, His, Leu, Arg
<220> FEATURE:
<221> NAME/KEY: MISC_FEATURE
<222> LOCATION: (12)..(12)
<223> OTHER INFORMATION: Xaa can be Arg, Lys, Trp

<400> SEQUENCE: 2

Xaa Xaa Xaa Trp Xaa Arg Xaa Xaa Xaa Lys Xaa Xaa
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Trp, Lys, Arg
<220> FEATURE:
<221> NAME/KEY: MISC_FEATURE
<222> LOCATION: (2)..(2)
<223> OTHER INFORMATION: Xaa can be Cys, Lys, Arg
<220> FEATURE:
<221> NAME/KEY: MISC_FEATURE
<222> LOCATION: (3)..(3)
<223> OTHER INFORMATION: Xaa can be Leu, Arg
<220> FEATURE:
<221> NAME/KEY: MISC_FEATURE
<222> LOCATION: (5)..(5)
<223> OTHER INFORMATION: Xaa can be Leu, Arg
<220> FEATURE:
<221> NAME/KEY: MISC_FEATURE
<222> LOCATION: (7)..(7)
<223> OTHER INFORMATION: Xaa can be Trp, Lys
<220> FEATURE:
<221> NAME/KEY: MISC_FEATURE
<222> LOCATION: (8)..(8)
<223> OTHER INFORMATION: Xaa can be Met, Trp
<220> FEATURE:
<221> NAME/KEY: MISC_FEATURE
<222> LOCATION: (9)..(9)
<223> OTHER INFORMATION: Xaa can be Arg, Val
<220> FEATURE:
<221> NAME/KEY: MISC_FEATURE
<222> LOCATION: (11)..(11)
<223> OTHER INFORMATION: Xaa can be Val, Ala, Arg
<220> FEATURE:
<221> NAME/KEY: MISC_FEATURE
<222> LOCATION: (12)..(12)
<223> OTHER INFORMATION: Xaa can be Arg, Leu

<400> SEQUENCE: 3

Xaa Xaa Xaa Trp Xaa Arg Xaa Xaa Xaa Lys Xaa Xaa
 1               5                  10

<210> SEQ ID NO 4
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Gln, Arg, Asn
<220> FEATURE:
<221> NAME/KEY: MISC_FEATURE
<222> LOCATION: (2)..(2)
```

```
<223> OTHER INFORMATION: Xaa can be Ser, Arg, Lys
<220> FEATURE:
<221> NAME/KEY: MISC_FEATURE
<222> LOCATION: (3)..(3)
<223> OTHER INFORMATION: Xaa can be Glu, Arg, Leu
<220> FEATURE:
<221> NAME/KEY: MISC_FEATURE
<222> LOCATION: (4)..(4)
<223> OTHER INFORMATION: Xaa can be Ala, Arg, Phe
<220> FEATURE:
<221> NAME/KEY: MISC_FEATURE
<222> LOCATION: (5)..(5)
<223> OTHER INFORMATION: Xaa can be Thr, Lys, Arg, His, Gln, Glu
<220> FEATURE:
<221> NAME/KEY: MISC_FEATURE
<222> LOCATION: (6)..(6)
<223> OTHER INFORMATION: Xaa can be Lys, Thr, Ser
<220> FEATURE:
<221> NAME/KEY: MISC_FEATURE
<222> LOCATION: (7)..(7)
<223> OTHER INFORMATION: Xaa can be Arg, Phe, Leu
<220> FEATURE:
<221> NAME/KEY: MISC_FEATURE
<222> LOCATION: (8)..(8)
<223> OTHER INFORMATION: Xaa can be Phe, Lys, Ala
<220> FEATURE:
<221> NAME/KEY: MISC_FEATURE
<222> LOCATION: (11)..(11)
<223> OTHER INFORMATION: Xaa can be Leu, Arg, Ala
<220> FEATURE:
<221> NAME/KEY: MISC_FEATURE
<222> LOCATION: (13)..(13)
<223> OTHER INFORMATION: Xaa can be Asn, Gln
<220> FEATURE:
<221> NAME/KEY: MISC_FEATURE
<222> LOCATION: (18)..(18)
<223> OTHER INFORMATION: Xaa can be Leu, Arg, Ala

<400> SEQUENCE: 4

Xaa Xaa Xaa Xaa Xaa Xaa Xaa Xaa Gln Trp Xaa Arg Xaa Leu Arg Lys
1               5                   10                  15

Val Xaa

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Gln, Arg, Asn
<220> FEATURE:
<221> NAME/KEY: MISC_FEATURE
<222> LOCATION: (3)..(3)
<223> OTHER INFORMATION: Xaa can be Glu, Arg, Leu
<220> FEATURE:
<221> NAME/KEY: MISC_FEATURE
<222> LOCATION: (4)..(4)
<223> OTHER INFORMATION: Xaa can be Ala, Arg, Phe
<220> FEATURE:
<221> NAME/KEY: MISC_FEATURE
<222> LOCATION: (5)..(5)
<223> OTHER INFORMATION: Xaa can be Thr, Lys, Arg, Gln, Glu
<220> FEATURE:
<221> NAME/KEY: MISC_FEATURE
<222> LOCATION: (6)..(6)
<223> OTHER INFORMATION: Xaa can be Lys, Thr, Ser
<220> FEATURE:
<221> NAME/KEY: MISC_FEATURE
<222> LOCATION: (7)..(7)
<223> OTHER INFORMATION: Xaa can be Arg, Phe, Leu
<220> FEATURE:
<221> NAME/KEY: MISC_FEATURE
<222> LOCATION: (8)..(8)
```

```
<223> OTHER INFORMATION: Xaa can be Phe, Lys, Ala
<220> FEATURE:
<221> NAME/KEY: MISC_FEATURE
<222> LOCATION: (11)..(11)
<223> OTHER INFORMATION: Xaa can be Leu, Arg, Ala
<220> FEATURE:
<221> NAME/KEY: MISC_FEATURE
<222> LOCATION: (18)..(18)
<223> OTHER INFORMATION: Xaa can be Leu, Arg, Ala

<400> SEQUENCE: 5

Xaa Ser Xaa Xaa Xaa Xaa Xaa Xaa Gln Trp Xaa Arg Asn Leu Arg Lys
1               5                   10                  15

Val Xaa

<210> SEQ ID NO 6
<211> LENGTH: 19
<212> TYPE: PRT
<213> ORGANISM: Artificial sequence
<220> FEATURE:
<223> OTHER INFORMATION: Synthetic peptide

<400> SEQUENCE: 6

Ser Gln Pro Glu Ala Thr Lys Cys Phe Gln Trp Gln Arg Asn Met Arg
1               5                   10                  15

Lys Val Arg

<210> SEQ ID NO 7
<211> LENGTH: 19
<212> TYPE: PRT
<213> ORGANISM: Artificial sequence
<220> FEATURE:
<223> OTHER INFORMATION: Synthetic peptide

<400> SEQUENCE: 7

Asn Gln Pro Thr Ala Thr Lys Cys Phe Gln Trp Gln Arg Asn Met Arg
1               5                   10                  15

Lys Val Arg

<210> SEQ ID NO 8
<211> LENGTH: 19
<212> TYPE: PRT
<213> ORGANISM: Artificial sequence
<220> FEATURE:
<223> OTHER INFORMATION: Synthetic peptide

<400> SEQUENCE: 8

Thr Gln Pro Asp Ala Thr Lys Cys Phe Gln Trp Gln Arg Asn Met Arg
1               5                   10                  15

Lys Val Arg

<210> SEQ ID NO 9
<211> LENGTH: 18
<212> TYPE: PRT
<213> ORGANISM: Artificial sequence
<220> FEATURE:
<223> OTHER INFORMATION: Synthetic peptide

<400> SEQUENCE: 9

Gln Pro Glu Ala Thr Lys Cys Phe Gln Trp Gln Arg Asn Met Arg Lys
1               5                   10                  15

Val Arg

<210> SEQ ID NO 10
```

```
<211> LENGTH: 18
<212> TYPE: PRT
<213> ORGANISM: Artificial sequence
<220> FEATURE:
<223> OTHER INFORMATION: Synthetic peptide

<400> SEQUENCE: 10

Gln Thr Glu Ala Asp Lys Cys Phe Gln Trp Gln Arg Asn Met Arg Lys
1               5                   10                  15

Val Arg

<210> SEQ ID NO 11
<211> LENGTH: 18
<212> TYPE: PRT
<213> ORGANISM: Artificial sequence
<220> FEATURE:
<223> OTHER INFORMATION: Synthetic peptide

<400> SEQUENCE: 11

Gln Asn Glu Ala Asp Lys Cys Phe Gln Trp Gln Arg Asn Met Arg Lys
1               5                   10                  15

Val Arg

<210> SEQ ID NO 12
<211> LENGTH: 18
<212> TYPE: PRT
<213> ORGANISM: Artificial sequence
<220> FEATURE:
<223> OTHER INFORMATION: Synthetic peptide

<400> SEQUENCE: 12

Gln Ser Glu Ala Glu Lys Cys Phe Gln Trp Gln Arg Asn Met Arg Lys
1               5                   10                  15

Val Arg

<210> SEQ ID NO 13
<211> LENGTH: 17
<212> TYPE: PRT
<213> ORGANISM: Artificial sequence
<220> FEATURE:
<223> OTHER INFORMATION: Synthetic peptide

<400> SEQUENCE: 13

Pro Glu Ala Thr Lys Cys Phe Gln Trp Gln Arg Asn Met Arg Lys Val
1               5                   10                  15

Arg

<210> SEQ ID NO 14
<211> LENGTH: 17
<212> TYPE: PRT
<213> ORGANISM: Artificial sequence
<220> FEATURE:
<223> OTHER INFORMATION: Synthetic peptide

<400> SEQUENCE: 14

Asn Glu Ala Asp Lys Cys Phe Gln Trp Gln Arg Asn Met Arg Lys Val
1               5                   10                  15

Arg

<210> SEQ ID NO 15
<211> LENGTH: 17
<212> TYPE: PRT
<213> ORGANISM: Artificial sequence
<220> FEATURE:
```

<223> OTHER INFORMATION: Synthetic peptide

<400> SEQUENCE: 15

Ser Glu Ala Glu Lys Cys Phe Gln Trp Gln Arg Asn Met Arg Lys Val
1               5                   10                  15

Arg

<210> SEQ ID NO 16
<211> LENGTH: 18
<212> TYPE: PRT
<213> ORGANISM: Artificial sequence
<220> FEATURE:
<223> OTHER INFORMATION: Synthetic peptide

<400> SEQUENCE: 16

Gln Ser Leu Ala Thr Lys Cys Phe Gln Trp Gln Arg Asn Met Arg Lys
1               5                   10                  15

Val Arg

<210> SEQ ID NO 17
<211> LENGTH: 18
<212> TYPE: PRT
<213> ORGANISM: Artificial sequence
<220> FEATURE:
<223> OTHER INFORMATION: Synthetic peptide

<400> SEQUENCE: 17

Gln Ser Glu Ala Thr Lys Leu Phe Gln Trp Gln Arg Asn Met Arg Lys
1               5                   10                  15

Val Arg

<210> SEQ ID NO 18
<211> LENGTH: 18
<212> TYPE: PRT
<213> ORGANISM: Artificial sequence
<220> FEATURE:
<223> OTHER INFORMATION: Synthetic peptide

<400> SEQUENCE: 18

Gln Ser Glu Ala Thr Lys Cys Phe Gln Trp Leu Arg Asn Met Arg Lys
1               5                   10                  15

Val Arg

<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

Gln Ser Leu Ala Thr Lys Leu Phe Gln Trp Leu Arg Asn Leu Arg Lys
1               5                   10                  15

Val Arg

<210> SEQ ID NO 20
<211> LENGTH: 18
<212> TYPE: PRT
<213> ORGANISM: Artificial sequence
<220> FEATURE:
<223> OTHER INFORMATION: Synthetic peptide

<400> SEQUENCE: 20

```
Gln Ser Glu Ala Thr Lys Leu Phe Gln Trp Gln Arg Asn Leu Arg Lys
1               5                   10                  15

Val Arg

<210> SEQ ID NO 21
<211> LENGTH: 18
<212> TYPE: PRT
<213> ORGANISM: Artificial sequence
<220> FEATURE:
<223> OTHER INFORMATION: Synthetic peptide

<400> SEQUENCE: 21

Gln Ser Leu Ala Glu Lys Leu Phe Gln Trp Leu Arg Asn Leu Arg Lys
1               5                   10                  15

Val Arg

<210> SEQ ID NO 22
<211> LENGTH: 18
<212> TYPE: PRT
<213> ORGANISM: Artificial sequence
<220> FEATURE:
<223> OTHER INFORMATION: Synthetic peptide

<400> SEQUENCE: 22

Gln Pro Glu Ala Thr Lys Cys Phe Pro Trp Gln Arg Asn Met Arg Lys
1               5                   10                  15

Val Arg

<210> SEQ ID NO 23
<211> LENGTH: 18
<212> TYPE: PRT
<213> ORGANISM: Artificial sequence
<220> FEATURE:
<223> OTHER INFORMATION: Synthetic peptide

<400> SEQUENCE: 23

Gln Ser Glu Ala Thr Lys Arg Phe Gln Trp Leu Arg Asn Leu Arg Lys
1               5                   10                  15

Val Leu

<210> SEQ ID NO 24
<211> LENGTH: 18
<212> TYPE: PRT
<213> ORGANISM: Artificial sequence
<220> FEATURE:
<223> OTHER INFORMATION: Synthetic peptide

<400> SEQUENCE: 24

Gln Ser Leu Ala Glu Lys Leu Phe Gln Trp Leu Arg Asn Arg Arg Lys
1               5                   10                  15

Val Arg

<210> SEQ ID NO 25
<211> LENGTH: 18
<212> TYPE: PRT
<213> ORGANISM: Artificial sequence
<220> FEATURE:
<223> OTHER INFORMATION: Synthetic peptide

<400> SEQUENCE: 25

Gln Ser Leu Ala Thr Lys Leu Phe Gln Trp Arg Arg Asn Leu Arg Lys
1               5                   10                  15

Val Arg
```

```
<210> SEQ ID NO 26
<211> LENGTH: 11
<212> TYPE: PRT
<213> ORGANISM: Artificial sequence
<220> FEATURE:
<223> OTHER INFORMATION: Synthetic peptide

<400> SEQUENCE: 26

Phe Gln Trp Lys Arg Ala Met Arg Lys Val Arg
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic peptide

<400> SEQUENCE: 27

Cys Phe Gln Trp Lys Arg Ala Met Arg Lys Val Arg
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic peptide

<400> SEQUENCE: 28

Phe Gln Trp Gln Arg Arg Ile Arg Lys Val Arg
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic peptide

<400> SEQUENCE: 29

Phe Gln Trp Arg Arg Ala Ile Arg Lys Val Arg
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic peptide

<400> SEQUENCE: 30

Trp Phe Gln Trp Gln Arg Asn Met Arg Lys Val Arg
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic peptide

<400> SEQUENCE: 31

Trp Phe Gln Trp Lys Arg Arg Met Arg Lys Val Arg
1               5                   10
```

```
<210> SEQ ID NO 32
<211> LENGTH: 11
<212> TYPE: PRT
<213> ORGANISM: Artificial sequence
<220> FEATURE:
<223> OTHER INFORMATION: Synthetic peptide

<400> SEQUENCE: 32

Phe Trp Trp Gln Arg Lys Met Arg Lys Val Arg
1               5                   10

<210> SEQ ID NO 33
<211> LENGTH: 11
<212> TYPE: PRT
<213> ORGANISM: Artificial sequence
<220> FEATURE:
<223> OTHER INFORMATION: Synthetic peptide

<400> SEQUENCE: 33

Phe Gln Trp Gln Arg Asn Met Arg Lys Val Arg
1               5                   10

<210> SEQ ID NO 34
<211> LENGTH: 11
<212> TYPE: PRT
<213> ORGANISM: Artificial sequence
<220> FEATURE:
<223> OTHER INFORMATION: Synthetic peptide

<400> SEQUENCE: 34

Phe Gln Trp Gln Arg Asn Ile Arg Lys Ile Arg
1               5                   10

<210> SEQ ID NO 35
<211> LENGTH: 11
<212> TYPE: PRT
<213> ORGANISM: Artificial sequence
<220> FEATURE:
<223> OTHER INFORMATION: Synthetic peptide

<400> SEQUENCE: 35

Phe Gln Trp Gln Arg Asn Leu Arg Lys Leu Arg
1               5                   10

<210> SEQ ID NO 36
<211> LENGTH: 11
<212> TYPE: PRT
<213> ORGANISM: Artificial sequence
<220> FEATURE:
<223> OTHER INFORMATION: Synthetic peptide

<400> SEQUENCE: 36

Phe Gln Trp Gln Arg Asn Ile Arg Lys Val Arg
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic peptide

<400> SEQUENCE: 37

Phe Gln Trp Gln Arg Pro Ile Arg Lys Val Arg
1               5                   10
```

```
<210> SEQ ID NO 38
<211> LENGTH: 11
<212> TYPE: PRT
<213> ORGANISM: Artificial sequence
<220> FEATURE:
<223> OTHER INFORMATION: Synthetic peptide

<400> SEQUENCE: 38

Phe Gln Trp Gln Pro Arg Ile Arg Lys Val Arg
1               5                   10

<210> SEQ ID NO 39
<211> LENGTH: 11
<212> TYPE: PRT
<213> ORGANISM: Artificial sequence
<220> FEATURE:
<223> OTHER INFORMATION: Synthetic peptide

<400> SEQUENCE: 39

Phe Gln Trp Arg Pro Gly Ile Arg Lys Leu Arg
1               5                   10

<210> SEQ ID NO 40
<211> LENGTH: 11
<212> TYPE: PRT
<213> ORGANISM: Artificial sequence
<220> FEATURE:
<223> OTHER INFORMATION: Synthetic peptide

<400> SEQUENCE: 40

Phe Gln Trp Lys Pro Ala Ile Arg Lys Val Arg
1               5                   10

<210> SEQ ID NO 41
<211> LENGTH: 12
<212> TYPE: PRT
<213> ORGANISM: Artificial sequence
<220> FEATURE:
<223> OTHER INFORMATION: Synthetic peptide

<400> SEQUENCE: 41

Cys Leu Asn Phe Lys Arg Gly Val Arg Lys Ile Arg
1               5                   10

<210> SEQ ID NO 42
<211> LENGTH: 12
<212> TYPE: PRT
<213> ORGANISM: Artificial sequence
<220> FEATURE:
<223> OTHER INFORMATION: Synthetic peptide

<400> SEQUENCE: 42

Cys Phe Gln Trp Gln Arg Lys Met Arg Lys Val Arg
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthetic peptide

<400> SEQUENCE: 43

Cys Phe Gln Trp Lys Arg Ala Met Arg Lys Val Arg
1               5                   10

<210> SEQ ID NO 44
```

<211> LENGTH: 12
<212> TYPE: PRT
<213> ORGANISM: Artificial sequence
<220> FEATURE:
<223> OTHER INFORMATION: Synthetic peptide

<400> SEQUENCE: 44

Cys Phe Lys Trp Lys Arg Lys Met Arg Lys Val Arg
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic peptide

<400> SEQUENCE: 45

Cys Phe Gln Trp Gln Lys Arg Met Lys Arg Val Lys
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Cys Phe Gln Trp Gln Arg Asn Met Arg Lys Val Arg
1               5                   10

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Glu Ala Thr Lys Cys Phe Gln Trp Gln Arg Asn Met Arg Lys Val Arg
1               5                   10                  15

<210> SEQ ID NO 48
<211> LENGTH: 18
<212> TYPE: PRT
<213> ORGANISM: Artificial sequence
<220> FEATURE:
<223> OTHER INFORMATION: Synthetic peptide

<400> SEQUENCE: 48

Gln Arg Glu Ala Arg Lys Arg Phe Gln Trp Leu Arg Asn Met Thr Lys
1               5                   10                  15

Val Arg

<210> SEQ ID NO 49
<211> LENGTH: 18
<212> TYPE: PRT
<213> ORGANISM: Artificial sequence
<220> FEATURE:
<223> OTHER INFORMATION: Synthetic peptide

<400> SEQUENCE: 49

Gln Glu Ser Ala Arg Lys Gln Phe Arg Trp Leu Arg Asn Leu Thr Lys
1               5                   10                  15

Val Leu

```
<210> SEQ ID NO 50
<211> LENGTH: 18
<212> TYPE: PRT
<213> ORGANISM: Artificial sequence
<220> FEATURE:
<223> OTHER INFORMATION: Synthetic peptide

<400> SEQUENCE: 50

Gln Arg Glu Ala Arg Lys Phe Arg Gln Trp Leu Arg Asn Met Thr Lys
1               5                   10                  15

Val Arg

<210> SEQ ID NO 51
<211> LENGTH: 18
<212> TYPE: PRT
<213> ORGANISM: Artificial sequence
<220> FEATURE:
<223> OTHER INFORMATION: Synthetic peptide

<400> SEQUENCE: 51

Gln Ser Glu Tyr Thr Lys Arg Tyr Gln Trp Leu Arg Asn Leu Arg Lys
1               5                   10                  15

Val Leu

<210> SEQ ID NO 52
<211> LENGTH: 18
<212> TYPE: PRT
<213> ORGANISM: Artificial sequence
<220> FEATURE:
<223> OTHER INFORMATION: Synthetic peptide

<400> SEQUENCE: 52

Gln Lys Arg Ala Thr Lys Arg Phe Gln Trp Leu Arg Asn Leu Arg Lys
1               5                   10                  15

Val Leu

<210> SEQ ID NO 53
<211> LENGTH: 18
<212> TYPE: PRT
<213> ORGANISM: Artificial sequence
<220> FEATURE:
<223> OTHER INFORMATION: Synthetic peptide

<400> SEQUENCE: 53

Gln Ser Glu Arg Lys Lys Arg Phe Gln Trp Leu Arg Asn Leu Arg Lys
1               5                   10                  15

Val Leu

<210> SEQ ID NO 54
<211> LENGTH: 18
<212> TYPE: PRT
<213> ORGANISM: Artificial sequence
<220> FEATURE:
<223> OTHER INFORMATION: Synthetic peptide

<400> SEQUENCE: 54

Gln Ser Arg Ala Thr Lys Arg Phe Gln Trp His Arg Asn Ala Arg Lys
1               5                   10                  15

Val Leu

<210> SEQ ID NO 55
<211> LENGTH: 18
```

```
<212> TYPE: PRT
<213> ORGANISM: Artificial sequence
<220> FEATURE:
<223> OTHER INFORMATION: Synthetic peptide

<400> SEQUENCE: 55

Gln Ser Arg Ala Thr Lys Arg Phe Gln Trp Leu Arg Asn His Arg Lys
1               5                   10                  15

Val Leu

<210> SEQ ID NO 56
<211> LENGTH: 18
<212> TYPE: PRT
<213> ORGANISM: Artificial sequence
<220> FEATURE:
<223> OTHER INFORMATION: Synthetic peptide

<400> SEQUENCE: 56

Gln Ser Leu Ala Arg Thr Phe Lys Gln Trp Ala Arg Asn Leu Arg Lys
1               5                   10                  15

Val Leu

<210> SEQ ID NO 57
<211> LENGTH: 18
<212> TYPE: PRT
<213> ORGANISM: Artificial sequence
<220> FEATURE:
<223> OTHER INFORMATION: Synthetic peptide

<400> SEQUENCE: 57

Gln Ser Ala Ala Arg Thr Phe Lys Gln Trp Ala Arg Asn Leu Arg Lys
1               5                   10                  15

Thr Leu

<210> SEQ ID NO 58
<211> LENGTH: 20
<212> TYPE: PRT
<213> ORGANISM: Artificial sequence
<220> FEATURE:
<223> OTHER INFORMATION: Synthetic peptide

<400> SEQUENCE: 58

Gln Ser Glu Ala Thr Lys Arg Phe Gln Trp Leu Arg Asn Leu Arg Lys
1               5                   10                  15

Val Leu Lys Arg
            20

<210> SEQ ID NO 59
<211> LENGTH: 20
<212> TYPE: PRT
<213> ORGANISM: Artificial sequence
<220> FEATURE:
<223> OTHER INFORMATION: Synthetic peptide

<400> SEQUENCE: 59

Gln Ser Glu Ala Thr Lys Arg Phe Gln Trp Leu Arg Asn Leu Arg Lys
1               5                   10                  15

Val Leu Trp Trp
            20

<210> SEQ ID NO 60
<211> LENGTH: 20
<212> TYPE: PRT
<213> ORGANISM: Artificial sequence
```

<220> FEATURE:
<223> OTHER INFORMATION: Synthetic peptide

<400> SEQUENCE: 60

Gln Ser Glu Ala Thr Lys Arg Phe Gln Trp Leu Arg Asn Leu Arg Lys
1               5                   10                  15

Val Leu Gly Pro
            20

<210> SEQ ID NO 61
<211> LENGTH: 20
<212> TYPE: PRT
<213> ORGANISM: Artificial sequence
<220> FEATURE:
<223> OTHER INFORMATION: Synthetic peptide

<400> SEQUENCE: 61

Val Ser Gln Ser Glu Ala Thr Lys Arg Phe Gln Trp Leu Arg Asn Leu
1               5                   10                  15

Arg Lys Val Leu
            20

<210> SEQ ID NO 62
<211> LENGTH: 20
<212> TYPE: PRT
<213> ORGANISM: Artificial sequence
<220> FEATURE:
<223> OTHER INFORMATION: Synthetic peptide

<400> SEQUENCE: 62

Lys Arg Gln Ser Leu Ala Arg Thr Phe Lys Gln Trp Ala Arg Asn Leu
1               5                   10                  15

Arg Lys Val Leu
            20

<210> SEQ ID NO 63
<211> LENGTH: 18
<212> TYPE: PRT
<213> ORGANISM: Artificial sequence
<220> FEATURE:
<223> OTHER INFORMATION: Synthetic peptide

<400> SEQUENCE: 63

Leu Val Lys Arg Leu Asn Arg Leu Trp Gln Phe Arg Lys Thr Ala Glu
1               5                   10                  15

Ser Gln

<210> SEQ ID NO 64
<211> LENGTH: 18
<212> TYPE: PRT
<213> ORGANISM: Artificial sequence
<220> FEATURE:
<223> OTHER INFORMATION: Synthetic peptide

<400> SEQUENCE: 64

Gln Ser Glu Ala Thr Lys Arg Phe Gln Trp Leu Arg Asn Leu Arg Lys
1               5                   10                  15

Val Leu

<210> SEQ ID NO 65
<211> LENGTH: 18
<212> TYPE: PRT
<213> ORGANISM: Artificial sequence
<220> FEATURE:

<223> OTHER INFORMATION: Synthetic peptide

<400> SEQUENCE: 65

Gln Ser Leu Ala His Ser Leu Phe Gln Trp Leu Arg Asn Leu Arg Lys
1               5                   10                  15

Val Arg

<210> SEQ ID NO 66
<211> LENGTH: 18
<212> TYPE: PRT
<213> ORGANISM: Artificial sequence
<220> FEATURE:
<223> OTHER INFORMATION: Synthetic peptide

<400> SEQUENCE: 66

Arg Ser Leu Ala Gln Lys Leu Phe Gln Trp Leu Arg Asn Leu Arg Lys
1               5                   10                  15

Val Arg

<210> SEQ ID NO 67
<211> LENGTH: 18
<212> TYPE: PRT
<213> ORGANISM: Artificial sequence
<220> FEATURE:
<223> OTHER INFORMATION: Synthetic peptide

<400> SEQUENCE: 67

Gln Ser Leu Ala Arg Lys Leu Phe Gln Trp Leu Arg Asn Leu Arg Lys
1               5                   10                  15

Val Ala

<210> SEQ ID NO 68
<211> LENGTH: 18
<212> TYPE: PRT
<213> ORGANISM: Artificial sequence
<220> FEATURE:
<223> OTHER INFORMATION: Synthetic peptide

<400> SEQUENCE: 68

Gln Ser Leu Ala Glu Lys Leu Phe Trp Gln Leu Arg Asn Leu Arg Lys
1               5                   10                  15

Val Arg

<210> SEQ ID NO 69
<211> LENGTH: 18
<212> TYPE: PRT
<213> ORGANISM: Artificial sequence
<220> FEATURE:
<223> OTHER INFORMATION: Synthetic peptide

<400> SEQUENCE: 69

Asn Ser Leu Phe Glu Lys Leu Ala Gln Trp Leu Arg Gln Leu Arg Lys
1               5                   10                  15

Val Arg

<210> SEQ ID NO 70
<211> LENGTH: 11
<212> TYPE: PRT
<213> ORGANISM: Artificial sequence
<220> FEATURE:
<223> OTHER INFORMATION: Synthetic peptide

<400> SEQUENCE: 70

```
Gly Arg Arg Arg Arg Ser Val Gln Trp Cys Ala
1               5                   10
```

<210> SEQ ID NO 71
<211> LENGTH: 18
<212> TYPE: PRT
<213> ORGANISM: Artificial sequence
<220> FEATURE:
<223> OTHER INFORMATION: Synthetic peptide

<400> SEQUENCE: 71

```
Gln Ser Glu Ala Thr Lys Cys Phe Leu Trp Arg Arg Asn Met Arg Lys
1               5                   10                  15

Val Arg
```

<210> SEQ ID NO 72
<211> LENGTH: 18
<212> TYPE: PRT
<213> ORGANISM: Artificial sequence
<220> FEATURE:
<223> OTHER INFORMATION: Synthetic peptide

<400> SEQUENCE: 72

```
Gln Ser Ala Lys Thr Ala Cys Phe Leu Trp Arg Arg Asn Met Arg Lys
1               5                   10                  15

Val Arg
```

<210> SEQ ID NO 73
<211> LENGTH: 12
<212> TYPE: PRT
<213> ORGANISM: Artificial sequence
<220> FEATURE:
<223> OTHER INFORMATION: Synthetic peptide

<400> SEQUENCE: 73

```
Cys Phe Leu Trp Arg Arg Asn Met Arg Lys Val Arg
1               5                   10
```

<210> SEQ ID NO 74
<211> LENGTH: 12
<212> TYPE: PRT
<213> ORGANISM: Artificial sequence
<220> FEATURE:
<223> OTHER INFORMATION: Synthetic peptide

<400> SEQUENCE: 74

```
Cys Phe Leu Trp Arg Arg Leu Met Arg Lys Leu Arg
1               5                   10
```

<210> SEQ ID NO 75
<211> LENGTH: 12
<212> TYPE: PRT
<213> ORGANISM: Artificial sequence
<220> FEATURE:
<223> OTHER INFORMATION: Synthetic peptide

<400> SEQUENCE: 75

```
Cys Arg Leu Trp Arg Arg Asn Met Arg Lys Val Arg
1               5                   10
```

<210> SEQ ID NO 76
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 76

Cys Trp Leu Trp Arg Arg Ala Met Arg Lys Val Trp
1               5                   10

<210> SEQ ID NO 77
<211> LENGTH: 12
<212> TYPE: PRT
<213> ORGANISM: Artificial sequence
<220> FEATURE:
<223> OTHER INFORMATION: Synthetic peptide

<400> SEQUENCE: 77

Leu Arg Leu Trp Arg Arg Leu Met Arg Lys Val Trp
1               5                   10

<210> SEQ ID NO 78
<211> LENGTH: 12
<212> TYPE: PRT
<213> ORGANISM: Artificial sequence
<220> FEATURE:
<223> OTHER INFORMATION: Synthetic peptide

<400> SEQUENCE: 78

Arg Arg Leu Trp Arg Arg Trp Met Arg Lys Val Leu
1               5                   10

<210> SEQ ID NO 79
<211> LENGTH: 12
<212> TYPE: PRT
<213> ORGANISM: Artificial sequence
<220> FEATURE:
<223> OTHER INFORMATION: Synthetic peptide

<400> SEQUENCE: 79

Cys Arg Leu Trp Arg Arg Arg Met Arg Lys Val Trp
1               5                   10

<210> SEQ ID NO 80
<211> LENGTH: 12
<212> TYPE: PRT
<213> ORGANISM: Artificial sequence
<220> FEATURE:
<223> OTHER INFORMATION: Synthetic peptide

<400> SEQUENCE: 80

Leu Arg Thr Trp Arg Arg Leu Thr Arg Lys Val Trp
1               5                   10

<210> SEQ ID NO 81
<211> LENGTH: 12
<212> TYPE: PRT
<213> ORGANISM: Artificial sequence
<220> FEATURE:
<223> OTHER INFORMATION: Synthetic peptide

<400> SEQUENCE: 81

Leu Arg Leu Trp Arg Arg Ser Met Arg Lys Val Trp
1               5                   10

<210> SEQ ID NO 82
<211> LENGTH: 12
<212> TYPE: PRT
<213> ORGANISM: Artificial sequence
<220> FEATURE:
<223> OTHER INFORMATION: Synthetic peptide
```

<400> SEQUENCE: 82

Cys Phe Leu Trp Arg Arg Ser Met Arg Arg Leu Arg
1               5                   10

<210> SEQ ID NO 83
<211> LENGTH: 11
<212> TYPE: PRT
<213> ORGANISM: Artificial sequence
<220> FEATURE:
<223> OTHER INFORMATION: Synthetic peptide

<400> SEQUENCE: 83

Cys Phe Leu Trp Arg Arg Leu Met Arg Lys Val
1               5                   10

<210> SEQ ID NO 84
<211> LENGTH: 11
<212> TYPE: PRT
<213> ORGANISM: Artificial sequence
<220> FEATURE:
<223> OTHER INFORMATION: Synthetic peptide

<400> SEQUENCE: 84

Arg Leu Trp Arg Arg Leu Met Arg Lys Val Arg
1               5                   10

<210> SEQ ID NO 85
<211> LENGTH: 16
<212> TYPE: PRT
<213> ORGANISM: Artificial sequence
<220> FEATURE:
<223> OTHER INFORMATION: Synthetic peptide

<400> SEQUENCE: 85

Arg Trp Cys Lys Leu Trp Arg Arg Leu Met Arg Lys Val Arg Arg Leu
1               5                   10                  15

<210> SEQ ID NO 86
<211> LENGTH: 16
<212> TYPE: PRT
<213> ORGANISM: Artificial sequence
<220> FEATURE:
<223> OTHER INFORMATION: Synthetic peptide

<400> SEQUENCE: 86

Arg Trp Cys Phe Leu Trp Arg Arg Leu Met Arg Lys His Arg Arg Leu
1               5                   10                  15

<210> SEQ ID NO 87
<211> LENGTH: 14
<212> TYPE: PRT
<213> ORGANISM: Artificial sequence
<220> FEATURE:
<223> OTHER INFORMATION: Synthetic peptide

<400> SEQUENCE: 87

Trp Cys Lys Leu Trp Arg Arg Leu Met Arg Lys Val Arg Arg
1               5                   10

<210> SEQ ID NO 88
<211> LENGTH: 15
<212> TYPE: PRT
<213> ORGANISM: Artificial sequence
<220> FEATURE:
<223> OTHER INFORMATION: Synthetic peptide

<400> SEQUENCE: 88

```
Thr Lys Cys Phe Leu Trp Arg Arg Asn Met Arg Lys Val Arg Gly
1               5                   10                  15

<210> SEQ ID NO 89
<211> LENGTH: 15
<212> TYPE: PRT
<213> ORGANISM: Artificial sequence
<220> FEATURE:
<223> OTHER INFORMATION: Synthetic peptide

<400> SEQUENCE: 89

Trp Phe Lys Cys Phe Gln Trp Gln Arg Asn Met Arg Lys Val Arg
1               5                   10                  15

<210> SEQ ID NO 90
<211> LENGTH: 12
<212> TYPE: PRT
<213> ORGANISM: Artificial sequence
<220> FEATURE:
<223> OTHER INFORMATION: Synthetic peptide

<400> SEQUENCE: 90

Lys Lys Leu Trp Arg Arg Trp Trp Arg Lys Val Leu
1               5                   10

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Val Trp Ile Val Lys Lys Gln Val Lys Arg Ile Lys
1               5                   10

<210> SEQ ID NO 92
<211> LENGTH: 12
<212> TYPE: PRT
<213> ORGANISM: Artificial sequence
<220> FEATURE:
<223> OTHER INFORMATION: Synthetic peptide

<400> SEQUENCE: 92

Leu Val Trp Ile Lys Arg His Ile Lys Lys Phe Lys
1               5                   10

<210> SEQ ID NO 93
<211> LENGTH: 12
<212> TYPE: PRT
<213> ORGANISM: Artificial sequence
<220> FEATURE:
<223> OTHER INFORMATION: Synthetic peptide

<400> SEQUENCE: 93

Trp Arg Arg Trp Leu Arg Lys Ser Val Lys Arg Leu
1               5                   10

<210> SEQ ID NO 94
<211> LENGTH: 12
<212> TYPE: PRT
<213> ORGANISM: Artificial sequence
<220> FEATURE:
<223> OTHER INFORMATION: Synthetic peptide

<400> SEQUENCE: 94
```

Trp Cys Arg Trp Leu Arg Lys Met Val Lys Ala Leu
1               5                   10

<210> SEQ ID NO 95
<211> LENGTH: 12
<212> TYPE: PRT
<213> ORGANISM: Artificial sequence
<220> FEATURE:
<223> OTHER INFORMATION: Synthetic peptide

<400> SEQUENCE: 95

Trp Arg Arg Trp Leu Arg Lys Met Val Lys Arg Leu
1               5                   10

<210> SEQ ID NO 96
<211> LENGTH: 11
<212> TYPE: PRT
<213> ORGANISM: Artificial sequence
<220> FEATURE:
<223> OTHER INFORMATION: Synthetic peptide

<400> SEQUENCE: 96

Gly Arg Arg Arg Arg Ser Val Gln Trp Cys Ala
1               5                   10

<210> SEQ ID NO 97
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: a fragment of human lactoferrin corresponding
      to amino acids 18-30

<400> SEQUENCE: 97

Lys Cys Phe Gln Trp Gln Arg Asn Met Arg Lys Val Arg
1               5                   10

SYNTHETIC PEPTIDES AND THEIR USE

CROSS-REFERENCE TO RELATED APPLICATIONS

This application is a U.S. National Stage patent application pursuant to 35 U.S.C. §371 of International Patent Application PCT/EP2012/051111, filed on Jan. 25, 2012, and published as WO 2012/101156 on Aug. 2, 2012, which claims priority to European Patent Application No. 11152213.2 filed on Jan. 26, 2011, the content of each is hereby expressly incorporated by reference in their entireties for all purposes.

FIELD OF THE INVENTION

The present invention relates to new peptides and to use thereof, in particular for treatment and/or prevention of infections, inflammations, pain, wounds, scar and/or tumours.

BACKGROUND ART

Lactoferrin is a single chain metal-binding glycoprotein with a molecular weight of 77 kDa. It has been found that the structural domain of lactoferrin responsible for the bactericidal properties is a pepsin-cleaved fragment called lactofericin (see e.g. Bellamy W., et al., Identification of the bactericidal domain of lactoferrin, Biochim. Biophys. Acta 1121: 130-136, 1992, and Bellamy W., et al., Antibacterial spectrum of lactoferricin B, a potent bactericidal peptide derived from the N-terminal region of bovine lactoferrin, J. Appl. Bact. 73: 472-479, 1992).

Lactoferrin receptors are found on many types of cells including monocytes and macrophages, lectin-stimulated human peripheral blood lymphocytes, brushborder cells, and tumour cell lines.

Several patent publications describe the possible use of lactoferrin for treatment of infections or inflammations. In WO 98/06425, e.g., it is disclosed that lactoferrin and lactoferricin can be used for treatment and prevention of infections, inflammations and tumours.

EP 629 347 describes an antimicrobial agent containing (A) lactoferrin hydrolysate and/or one or more of antimicrobial peptides derived from lactoferrins, and (B) one or more compounds selected from the group consisting of metal-chelating protein, tocopherol, cyclodextrin, glycerine-fatty acid ester, alcohol, EDTA or a salt thereof, ascorbic acid or a salt thereof, citric acid or a salt thereof, polyphosphoric acid or a salt thereof, chitosan, cysteine, and cholic acid as the effective components thereof. This antimicrobial agent is intended for treatment of products, and especially for safely treating e.g. food and medicines. The agent according to this publication is thus a new preservative. In the publication several peptide sequences are given and some of them resemble the peptides according to the invention, although there are several important differences described further below.

U.S. Pat. No. 5,304,633 discloses antimicrobial peptides isolated from hydrolysates of human and bovine lactoferrin. Isolation of peptides corresponding to amino acids 12 to 47, and 17 to 41 of human lactoferrin are specifically disclosed.

JP 7145196 describes the preparation of antibiotic peptides by hydrolysis of lactoferrin. The preparation of a peptide corresponding to amino acids 17 to 41 of human lactoferrin is specifically described.

JP 8040925 discloses pharmaceutical compositions containing lactoferrin derived peptides and their use in the treatment of cornea damages, especially keratitis. Peptides corresponding to amino acids 17 to 41, 12 to 58, and 19 to 38, of human lactoferrin are specifically disclosed.

JP 7274970 describes the recombinant production of antibacterial lactoferricin derived peptides, specifically a peptides corresponding to amino acids 18 to 42 of human lactoferrin is disclosed.

JP 8143468 describes lactoferrin derived peptides and their use as antiulcer drugs, a peptide corresponding to amino acids 19 to 33 of human lactoferrin is specifically disclosed.

WO 00/01730 describes peptides derived from human lactoferrin and their use for treatment of infections and inflammations.

EP 1 228 097 describes peptides derived from the immediate N-terminal end of human lactoferrin and their use as microbial agents.

EP 1151009 describes peptides comprising a sequence corresponding to amino acids 35 to 50 of human lactoferrin having antimicrobial and/or endotoxin neutralizing activity.

WO 2006/047744 describes immunomodulatory peptides derived from the N-terminal part of human lactoferrin comprising at least 33 amino acids and being substituted in both the N- and C-terminus with four positively charged amino acids.

WO 2009/050279 describes mutated lactoferrin peptides and their antimicrobial activity.

WO 2009/062898 describes arginine substituted lactoferrin peptides and their antimicrobial and anti-inflammatory activity.

SUMMARY OF THE INVENTION

The present invention relates to new peptides with improved antimicrobial and/or anti-inflammatory activity. The peptides according to the present invention are designed based on the amino acid sequence SEQ ID NO:1 corresponding to amino acids 13 to 30 of mature human lactoferrin.

```
                                              (SEQ ID NO: 1)
        Q-P-E-A-T-K-C-F-Q-W-Q-R-N-M-R-K-V-R
```

The first embodiment of the invention relates to peptides comprising at least the amino acid sequence

```
                                              (SEQ ID NO: 2)
        X1-X2-X3-W-X5-R-X7-X8-X9-K-X11-X12
``` wherein

X1 is C, L, W, K or R

X2 is C, F, K, W or R

X3 is L or R

X5 is L, K or R

X7 is N, S, A, L, W, K or R

X8 is M, W or S

X9 is R or V

X11 is V, A, H, L, or R, and

X12 is R, L or W and functional equivalent variants of these peptides.

The peptides can preferably further comprise the amino acids W or R-W at the N-terminal end.

The peptides can preferably further comprise the amino acids R or R-L at the C-terminal end.

Preferably the peptides according to the first embodiment of the invention comprise at least the amino acid sequence

```
                                             (SEQ ID NO: 3)
        X1-X2-X3-W-X5-R-X7-X8-X9-K-X11-X12
``` wherein
X1 is W, K or R
X2 is C, K, or R
X3 is L, or R
X5 is L, or R
X7 is W, or K
X8 is M, or W
X9 is R, or V
X11 is V, A, or R, and
X12 is R, or L
and functional equivalent variants of these peptides.

The peptides can preferably further comprise the amino acids W or R-W at the N-terminal end.

The peptides can preferably further comprise the amino acids R or R-L at the C-terminal end.

More preferably, the peptides according to the first embodiment of the invention are selected from peptides comprising an amino acid sequence selected from the amino acid sequences

```
                                         (SEQ ID NO: 74)
        C-F-L-W-R-R-L-M-R-K-L-R (SEQ ID NO: 76)
        C-W-L-W-R-R-A-M-R-K-V-W (SEQ ID NO: 77)
        L-R-L-W-R-R-L-M-R-K-V-W (SEQ ID NO: 78)
        R-R-L-W-R-R-W-M-R-K-V-L (SEQ ID NO: 79)
        C-R-L-W-R-R-R-M-R-K-V-W (SEQ ID NO: 81)
        L-R-L-W-R-R-S-M-R-K-V-W (SEQ ID NO: 90)
        K-K-L-W-R-R-W-W-R-K-V-L (SEQ ID NO: 85)
        R-W-C-K-L-W-R-R-L-M-R-K-V-R-R-L (SEQ ID NO: 86)
        R-W-C-F-L-W-R-R-L-M-R-K-H-R-R-L (SEQ ID NO: 87)
        W-C-K-L-W-R-R-L-M-R-K-V-R-R (SEQ ID NO: 93)
        W-R-R-W-L-R-K-S-V-K-R-L (SEQ ID NO: 94)
        W-C-R-W-L-R-K-M-V-K-A-L (SEQ ID NO: 95)
        W-R-R-W-L-R-K-M-V-K-R-L
``` and functional equivalent variants of these peptides.

Most preferably the peptides according to the first embodiment of the invention are selected from the peptides;

```
                                         (SEQ ID NO: 74)
        C-F-L-W-R-R-L-M-R-K-L-R (SEQ ID NO: 76)
        C-W-L-W-R-R-A-M-R-K-V-W (SEQ ID NO: 77)
        L-R-L-W-R-R-L-M-R-K-V-W (SEQ ID NO: 78)
        R-R-L-W-R-R-W-M-R-K-V-L (SEQ ID NO: 79)
        C-R-L-W-R-R-R-M-R-K-V-W (SEQ ID NO: 81)
        L-R-L-W-R-R-S-M-R-K-V-W (SEQ ID NO: 90)
        K-K-L-W-R-R-W-W-R-K-V-L (SEQ ID NO: 85)
        R-W-C-K-L-W-R-R-L-M-R-K-V-R-R-L (SEQ ID NO: 86)
        R-W-C-F-L-W-R-R-L-M-R-K-H-R-R-L (SEQ ID NO: 87)
        W-C-K-L-W-R-R-L-M-R-K-V-R-R (SEQ ID NO: 93)
        W-R-R-W-L-R-K-S-V-K-R-L (SEQ ID NO: 94)
        W-C-R-W-L-R-K-M-V-K-A-L (SEQ ID NO: 95)
        W-R-R-W-L-R-K-M-V-K-R-L
``` and functional equivalent variants of these peptides.

The second embodiment of the invention relates to peptides comprising at least the amino acid sequence

```
                                                  (SEQ ID NO: 4)
    X1-X2-X3-X4-X5-X6-X7-X8-Q-W-X11-R-X13-L-R-K-V-X18
``` wherein
X1 is Q, R, or N
X2 is S, R, or K
X3 is E, R, or L
X4 is A, R, or F
X5 is T, K, R, H, Q, or E
X6 is K, T or S
X7 is R, F or L
X8 is F, K, or A
X11 is L, R, or A
X13 is N, or Q, and
X18 is L, R or A
and functional equivalent variants of these peptides.

The peptides can preferably further comprise the amino acid sequence K-R at the N-terminal end.

The peptides can preferably further comprise the amino acid sequence K-R, W-W, or G-P at the C-terminal end.

Preferably the peptides according to the second embodiment of the invention comprise at least the amino acid sequence

```
                                                  (SEQ ID NO: 5)
    X1-S-X3-X4-X5-X6-X7-X8-Q-W-X11-R-N-L-R-K-V-X18
``` wherein
X1 is Q, R, or N
X3 is E, R, or L
X4 is A, R, or F
X5 is T, K, R, Q, or E
X6 is K, T or S
X7 is R, F or L
X8 is F, K, or A X11 is L, R, or A, and
X18 is L, R or A
and functional equivalent variants of these peptides.

The peptides can preferably further comprise the amino acid sequence K-R at the N-terminal end.

The peptides can preferably further comprise the amino acid sequence K-R, W-W, or G-P at the C-terminal end.

More preferably, the peptides according to the second embodiment of the invention are selected from peptides comprising an amino acid sequence selected from the amino acid sequences

```
                                           (SEQ ID NO: 19)
       Q-S-L-A-T-K-L-F-Q-W-L-R-N-L-R-K-V-R (SEQ ID NO: 21)
       Q-S-L-A-E-K-L-F-Q-W-L-R-N-L-R-K-V-R (SEQ ID NO: 23)
       Q-S-E-A-T-K-R-F-Q-W-L-R-N-L-R-K-V-L (SEQ ID NO: 25)
       Q-S-L-A-T-K-L-F-Q-W-R-R-N-L-R-K-V-R (SEQ ID NO: 52)
       Q-K-R-A-T-K-R-F-Q-W-L-R-N-L-R-K-V-L (SEQ ID NO: 53)
       Q-S-E-R-K-K-R-F-Q-W-L-R-N-L-R-K-V-L (SEQ ID NO: 56)
       Q-S-L-A-R-T-F-K-Q-W-A-R-N-L-R-K-V-L (SEQ ID NO: 58)
       Q-S-E-A-T-K-R-F-Q-W-L-R-N-L-R-K-V-L-K-R (SEQ ID NO: 59)
       Q-S-E-A-T-K-R-F-Q-W-L-R-N-L-R-K-V-L-W-W (SEQ ID NO: 60)
       Q-S-E-A-T-K-R-F-Q-W-L-R-N-L-R-K-V-L-G-P (SEQ ID NO: 62)
       K-R-Q-S-L-A-R-T-F-K-Q-W-A-R-N-L-R-K-V-L (SEQ ID NO: 65)
       Q-S-L-A-H-S-L-F-Q-W-L-R-N-L-R-K-V-R (SEQ ID NO: 66)
       R-S-L-A-Q-K-L-F-Q-W-L-R-N-L-R-K-V-R (SEQ ID NO: 67)
       Q-S-L-A-R-K-L-F-Q-W-L-R-N-L-R-K-V-A (SEQ ID NO: 69)
       N-S-L-F-E-K-L-A-Q-W-L-R-Q-L-R-K-V-R
``` and functional equivalent variants of these peptides.

Most preferably the peptides according to the second embodiment of the invention are selected from the peptides

```
                                           (SEQ ID NO: 19)
       Q-S-L-A-T-K-L-F-Q-W-L-R-N-L-R-K-V-R (SEQ ID NO: 21)
       Q-S-L-A-E-K-L-F-Q-W-L-R-N-L-R-K-V-R (SEQ ID NO: 23)
       Q-S-E-A-T-K-R-F-Q-W-L-R-N-L-R-K-V-L (SEQ ID NO: 25)
       Q-S-L-A-T-K-L-F-Q-W-R-R-N-L-R-K-V-R (SEQ ID NO: 52)
       Q-K-R-A-T-K-R-F-Q-W-L-R-N-L-R-K-V-L (SEQ ID NO: 53)
       Q-S-E-R-K-K-R-F-Q-W-L-R-N-L-R-K-V-L (SEQ ID NO: 56)
       Q-S-L-A-R-T-F-K-Q-W-A-R-N-L-R-K-V-L (SEQ ID NO: 58)
       Q-S-E-A-T-K-R-F-Q-W-L-R-N-L-R-K-V-L-K-R (SEQ ID NO: 59)
       Q-S-E-A-T-K-R-F-Q-W-L-R-N-L-R-K-V-L-W-W (SEQ ID NO: 60)
       Q-S-E-A-T-K-R-F-Q-W-L-R-N-L-R-K-V-L-G-P (SEQ ID NO: 62)
       K-R-Q-S-L-A-R-T-F-K-Q-W-A-R-N-L-R-K-V-L (SEQ ID NO: 65)
       Q-S-L-A-H-S-L-F-Q-W-L-R-N-L-R-K-V-R (SEQ ID NO: 66)
       R-S-L-A-Q-K-L-F-Q-W-L-R-N-L-R-K-V-R (SEQ ID NO: 67)
       Q-S-L-A-R-K-L-F-Q-W-L-R-N-L-R-K-V-A (SEQ ID NO: 69)
       N-S-L-F-E-K-L-A-Q-W-L-R-Q-L-R-K-V-R
``` and functional equivalent variants of these peptides.

Additional preferred peptides according to the invention are

```
                                           (SEQ ID NO: 14)
              N-E-A-D-K-C-F-Q-W-Q-R-N-M-R-K-V-R (SEQ ID NO: 16)
              Q-S-L-A-T-K-C-F-Q-W-Q-R-N-M-R-K-V-R (SEQ ID NO: 18)
              Q-S-E-A-T-K-C-F-Q-W-L-R-N-M-R-K-V-R (SEQ ID NO: 24)
              Q-S-L-A-E-K-L-F-Q-W-L-R-N-R-R-K-V-R (SEQ ID NO: 31)
              W-F-Q-W-K-R-R-M-R-K-V-R (SEQ ID NO: 32)
              F-W-W-Q-R-K-M-R-K-V-R (SEQ ID NO: 84)
              R-L-W-R-R-L-M-R-K-V-R
``` and functional equivalent variants of these peptides.

The peptides according to the invention preferably have a length of from 12 to 100 amino acid residues, such as preferably a length of from 12 to 50 amino acid residues, or a length of from 12 to 30 amino acid residues, such as more preferably a length of from 12 to about 25 amino acid residues, such as most preferably a length of from 12 to 20 amino acid residues, such as 12, 13, 14, 15, 16, 17, 18, 19 or 20 amino acid residues.

The peptides according to the invention comprise the standard twenty genetically-encoded amino acids. They may also comprise one or more of the amino acids in their corresponding stereoisomers in the 'D' form, as compared to the natural 'L' form.

In the description single-letter or three-letter symbols are used to denote the amino acids. These symbols, which are well known to man skilled in the art, have the following meaning: A=Ala=alanine, C=Cys=cysteine, D=Asp=aspartic acid, E=Glu=glutamic acid, F=Phe=phenylalanine, G=Gly=glycine, I—Ile=isoleucine, K=Lys=lysine, M=Met=methionine, N=Asn=asparagine, P=Pro=proline, Q=Gln=glutamine, R=Arg=arginine, S=Ser=serine, T=Thr=threonine, V=Val=valine, W=Trp=tryptophan.

Lower case letters are used to designate the corresponding D-amino acids.

Functional equivalent variants of the peptides according to the invention can include insertions or deletions of one or more amino acids, such as 1-5 insertions or deletions, 1, 2, 3, 4 or 5 insertions or deletions.

Functional equivalent variants of the peptides according to the invention can also include substitutions. Substitutions can be either conservative or non-conservative. Conservative substitutions are substitution of an amino acid within the same general class (e.g. an acidic amino acid, a basic amino acid, etc.) by another amino acid within the same class. E.g. a hydrophobic amino acid can be substituted with another hydrophobic amino acid, e.g. Trp can be substituted for Leu. A positively charged amino acid can be substituted with another positively charged amino acid, e.g. Arg can be substituted for Lys, such as 1-5 substitutions, 1, 2, 3, 4 or 5 substitutions.

FIG. 1 illustrates the different classes of amino acids.

The functional equivalent variants of the peptides according to the invention can also comprise other unnatural amino acids, as long as the desired functional property is retained by the polypeptide. Such unnatural amino acids can include α,α-disubstituted amino acids, N-alkyl amino acids or other variants mimicking a specific natural amino acid.

E.g. in the functional equivalent variants of the peptides according to the invention lysine (K/Lys) can preferably be substituted by Dap (diaminopropionic acid), Dab (2,4-diaminobutanoic acid), Orn (ornithine) or Hyl (5-Hydroxylysine), arginine (R/Arg) can preferably be substituted by Har (homoarginine), alanine (A/Ala) can preferably be substituted by Aib (α-Aminoisobutyric acid) or Abu (2-Aminobutanoic acid), valine (V/Val) can preferably be substituted by Nva (norvaline) or Iva (isovaline), leucine (L/Leu) can preferably be substituted by Nle (norleucine) or Cha (3-Cyclohexylalanine), serine (S/Ser) can preferably be substituted by Hse (Homoserine), cysteine (C/Cys) can preferably be substituted by Hcy (Homocysteine), histidine (H/His) can preferably be substituted by Hhs (Homohistidine) or 3-MH (3-methylhistidine), phenylalanine (F/Phe) can preferably be substituted with Phg (2-Phenylglycine), proline (P/Pro) can preferably be substituted with Hyp (4-hydroxyproline).

Accordingly, functionally equivalent variants of the peptides are peptides that have more than 70% sequence identity, such as more than 75% sequence identity, preferably more than 80% sequence identity such as more than 85% sequence identity, most preferably more than 90% sequence identity such as more than 93, 94, 95, 96, 97, 98, or 99% sequence identity, compared to a peptide selected from the peptides

```
                                            (SEQ ID NO: 74)
C-F-L-W-R-R-L-M-R-K-L-R (SEQ ID NO: 76)
C-W-L-W-R-R-A-M-R-K-V-W (SEQ ID NO: 77)
L-R-L-W-R-R-L-M-R-K-V-W (SEQ ID NO: 78)
R-R-L-W-R-R-W-M-R-K-V-L (SEQ ID NO: 79)
C-R-L-W-R-R-R-M-R-K-V-W
```

-continued
```
                                            (SEQ ID NO: 81)
L-R-L-W-R-R-S-M-R-K-V-W (SEQ ID NO: 90)
K-K-L-W-R-R-W-W-R-K-V-L (SEQ ID NO: 85)
R-W-C-K-L-W-R-R-L-M-R-K-V-R-R-L (SEQ ID NO: 86)
R-W-C-F-L-W-R-R-L-M-R-K-H-R-R-L (SEQ ID NO: 87)
W-C-K-L-W-R-R-L-M-R-K-V-R-R (SEQ ID NO: 93)
W-R-R-W-L-R-R-K-S-V-K-R-L (SEQ ID NO: 94)
W-C-R-W-L-R-K-M-V-K-A-L (SEQ ID NO: 95)
W-R-R-W-L-R-K-M-V-K-R-L (SEQ ID NO: 19)
Q-S-L-A-T-K-L-F-Q-W-L-R-N-L-R-K-V-R (SEQ ID NO: 21)
Q-S-L-A-E-K-L-F-Q-W-L-R-N-L-R-K-V-R (SEQ ID NO: 23)
Q-S-E-A-T-K-R-F-Q-W-L-R-N-L-R-K-V-L (SEQ ID NO: 25)
Q-S-L-A-T-K-L-F-Q-W-R-R-N-L-R-K-V-R (SEQ ID NO: 52)
Q-K-R-A-T-K-R-F-Q-W-L-R-N-L-R-K-V-L (SEQ ID NO: 53)
Q-S-E-R-K-K-R-F-Q-W-L-R-N-L-R-K-V-L (SEQ ID NO: 56)
Q-S-L-A-R-T-F-K-Q-W-A-R-N-L-R-K-V-L (SEQ ID NO: 58)
Q-S-E-A-T-K-R-F-Q-W-L-R-N-L-R-K-V-L-K-R (SEQ ID NO: 59)
Q-S-E-A-T-K-R-F-Q-W-L-R-N-L-R-K-V-L-W-W (SEQ ID NO: 60)
Q-S-E-A-T-K-R-F-Q-W-L-R-N-L-R-K-V-L-G-P (SEQ ID NO: 62)
K-R-Q-S-L-A-R-T-F-K-Q-W-A-R-N-L-R-K-V-L (SEQ ID NO: 65)
Q-S-L-A-H-S-L-F-Q-W-L-R-N-L-R-K-V-R (SEQ ID NO: 66)
R-S-L-A-Q-K-L-F-Q-W-L-R-N-L-R-K-V-R (SEQ ID NO: 67)
Q-S-L-A-R-K-L-F-Q-W-L-R-N-L-R-K-V-A (SEQ ID NO: 69)
N-S-L-F-E-K-L-A-Q-W-L-R-Q-L-R-K-V-R (SEQ ID NO: 14)
N-E-A-D-K-C-F-Q-W-Q-R-N-M-R-K-V-R (SEQ ID NO: 16)
Q-S-L-A-T-K-C-F-Q-W-Q-R-N-M-R-K-V-R (SEQ ID NO: 18)
Q-S-E-A-T-K-C-F-Q-W-L-R-N-M-R-K-V-R (SEQ ID NO: 24)
Q-S-L-A-E-K-L-F-Q-W-L-R-N-R-R-K-V-R
```

```
W-F-Q-W-K-R-M-R-K-V-R                    (SEQ ID NO: 31)

F-W-W-Q-R-K-M-R-K-V-R                    (SEQ ID NO: 32)

R-L-W-R-R-L-M-R-K-V-R                    (SEQ ID NO: 84)
```

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:1 (the length of the sequence set forth in SEQ ID NO:1 is 18) and the number of matches is 16, then the sequence has a percent identity of 89% (i.e., 16÷18*100=89) to the sequence set forth in SEQ ID NO:1.

Furthermore, fusions of the peptides according to the invention to other polypeptides, e.g. glutathione-S-transferase, protein A, oligo-histidine tag to simplify purification, or to an epitope recognised by an antibody such as the Myc tag epitope are also included in the present invention.

Fusions that include other desirable features that are, for example, useful in detecting or isolating the peptide, or promoting cellular uptake of the peptide are also included in the invention. Examples of such fusion partners are a biotin moiety, a streptavidin moiety, a radioactive moiety, a fluorescent moiety like a small fluorophore or a green fluorescent protein GFP fluorophore, an immunogenic tag, a lipophilic molecule or polypeptide domain that is capable of promoting cellular uptake of the peptide.

Functional equivalent variants of the peptides according to the invention can also comprise chemically modified or derivatised amino acids, for example by PEGylation, amidation, esterification, acylation, acetylation and/or alkylation.

Different attachments strategies for PEG exist and should be included. For example, PEG can be linked to N-terminal amino groups, or to amino acid residues with reactive amino or hydroxyl groups (Lys, His, Ser, Thr and Tyr) directly or by using γ-amino butyric acid as linkers. PEG can also be coupled to carboxyl (Asp, Glu, C-terminal) or sulfhydryl (Cys) groups.

Functional equivalent variants of the peptides according to the invention can also comprise chemical derivatives of the amino acids created by reaction with a functional side. Such derivatised molecules include molecules in which free amino groups have been derivatised to form amine hydrochlorides, p-toluene sulphonyl groups, carboxybenzoxy groups, t-butyl-oxycarbonyl groups, chloroacetyl groups or formyl groups. Free carboxyl groups can be derivatised to form salts, methyl and ethyl esters or other types of esters and hydrazides. Free hydroxyl groups can be derivatised to form O-acyl or O-alkyl derivatives.

Functional equivalent variants of the peptides according to the invention can also comprise peptidomimetic variants of the peptides. A peptidomimetic is a compound that mimics the conformation and particular features of the peptide. For example, peptidomimetics include peptides with reversed (—CO—NH—) linkages. In addition, peptidomimetics include variants where the amino acid residues are linked by a γ(CH$_2$NH)-bond that replaces the conventional amide linkage. Furthermore, peptidomimetics also include omega-amino acids, where the amino- and carboxyl-groups are separated by polymethylene units of variable length.

The peptides according to the invention can include modifications such as amidation, amino terminal acylation (e.g. acetylation or thioglycolic acid amidation), terminal carboxylamidation (e.g. with ammonia or methylamine), and other terminal modifications there the peptide's N- or C-terminal regions are blocked to help reduce susceptibility to exoproteolytic digestion. Further, by acetylation of the N-terminal into and amidation of the C-terminal, the peptides will be uncharged at the ends. Assuming that receptors bind the corresponding sequences of LF (where there are no N- and C-terminal charges), the capped peptides should bind better as they in this respect resemble the native protein more than uncapped peptides.

The peptides according to the invention can be C-terminally end-tagged with Tryptophan to increase potency, as described by Pasupuleti et al. Biochim Biophys Acta 2009, 1790:800-8.

Further, if present, a cysteine residue in the peptides can be replaced by an acetamidomethyl-cysteine. Further, the peptides according to the invention can be in a cyclic form, obtained by creation of a disulphide bridge between two cysteines in the sequence. Further, peptides according to the invention can include formed lactams.

The peptides according to the invention are suitable for treatment and/or prevention of infections, inflammations, tumours, pain, wounds, and/or scars. The term "treatment" used herein refers to curing, reversing, attenuating, alleviating, minimising, suppressing or halting the deleterious effects of a disease state, disease progression or other abnormal condition, and the term "prevention" used herein refers to minimising, reducing or suppressing the risk of developing a disease state or progression or other abnormal or deleterious conditions.

The infections treatable with the peptides or medicinal products or medical devices according to the invention include infections caused by all kinds of pathogens, such as bacteria, viruses, fungi, etc. The peptides according to the invention may be used to coat/treat different medical device products for reducing/preventing device-related infections It is also possible to treat different types of inflammations. Inflammation is a complex phenomenon marked i.a. by abnormal "redness" and swelling of tissues and organs, pain and heat in affected areas, capillary dilation, leucocyte infiltration, etc. Inflammation is primarily caused by exposure to bacterial and other noxious agents and physical injury. Allergic inflammation is an important pathophysiological feature of several disabilities or medical conditions including allergic asthma, atopic dermatitis, allergic rhinitis and several ocular allergic diseases.

Accordingly, one aspect of the present invention provides methods for treatment and/or prevention of infections, inflammations, tumours, pain, wounds and scars wherein an effective amount of a peptide of the invention, and functionally equivalent variants thereof, is administered to a patient. Said peptide may be formulated for orally, systemically, parenterally, locally or topically administered. Further, said peptide may be included in food stuff or included in an infant formula food.

Further, another aspect of the present invention provides peptides of the invention for use in the treatment and/or prevention of infections, inflammations, tumours, pain, wounds and scars. Said peptide may be formulated for oral administration, systemic administration, parenteral administration, local administration or topical administration. Further, said peptide for use may be included in food stuff or included in an infant formula food.

Further, another aspect of the present invention provides use the peptides of the invention, for the production of a medicinal product or medical device for treatment and/or prevention of infections, inflammations, tumours, pain, wounds and scars. Said medicinal product may be formulated for oral administration, systemic administration, parenteral administration, local administration or topical administration. Further, medicinal product or medical product/medical device may be included in food stuff or included in an infant formula food.

Inflammation has many forms and is mediated by a variety of different cytokines and other chemical signals. These mediators of inflammation include tumour necrosis factor-α (TNF-α), interleukin-1 (IL-1), interleukin-4 (IL-4), interleukin-5 (IL-5), interleukin-6 (IL-6), interleukin-8 (IL-8), interferon-gamma (IFN-γ) and various colony-stimulating factors (CSFs).

Though inhibition of infections and modulation of inflammatory response, the peptides are suitable for treatment and/or prevention of wounds and/or scar formation. As stated above, the peptides according to the invention are also suitable for treatment of tumours.

The peptides according to the invention may either be used as they are or be included in a medical device, medicinal product or a pharmaceutical composition. The medicinal product or medical device or a pharmaceutical composition according to the invention may also comprise substances used to facilitate the production of the pharmaceutical preparation or the administration of the preparations. Such substances are well known to people skilled in the art and may for example be pharmaceutically acceptable adjuvants, carriers and preservatives.

Accordingly, one aspect of the present invention provides pharmaceutical compositions comprising a peptide according to the invention.

Another aspect of the invention provides pharmaceutical compositions comprising a peptide according to the invention for use in treatment and/or prevention of infections, inflammations, tumours, pain, wounds and scars.

The peptides according to the invention may either be formulated for oral administration, systemic administration, parenteral administration, local administration or topical administration.

The peptides, medicinal products, medical device and pharmaceutical composition according to the invention can be administered to a patient either orally, systemically, parenterally, locally or topically.

The term "patient" used herein relates to any person at risk for or suffering from a disease state, disease progression or other abnormal or deleterious condition.

The systemic administration is suitable e.g. for treatment of urinary tract infection, colitis and tumours. The systemic administration can be undertaken by oral, nasal, pulmonary, oropharyngeal, intravenous, intraartery, intracavitary, intramuscular, subcutaneous, transdermal, suppositories (including rectal) or other routes known to those of skill in the art.

The local administration is suitable e.g. for treatment of skin and skin structure infections and inflammations, respiratory infections, all infections and inflammations in mucosal membranes etc. The local administration can be undertaken by topical, epicutaneous, oral, nasal, vaginal, ophthalmic, otic, pulmonary or oropharyngeal route. For treatment of local infections or inflammations the peptides or medicinal products according to the invention may e.g. be included in a gel, a cream, an ointment, solution or a paste, an inhalation powder/solution, an otic or ophthalmic solution/suspension/ointment.

In the method according to the invention an effective amount of a peptide according to the invention is administered to a patient. The term "effective amount" used herein relates to an amount sufficient to treat or prevent a disease state, disease progression or other abnormal or deleterious conditions.

The peptides or medicinal products or medical device and methods according to the invention are particularly well suited for treatment and/or prevention of urinary tract infection and colitis, skin and skin structure infections and inflammation, infections and inflammation in outer ear, ear canal, inner ear and eye and respiratory system, chronic and acute wounds, but several other inflammatory and infectious diseases are also treatable according to the present invention, such as inflammatory bowel diseases, rheumatoid arthritis, arthrosis, conditions caused by the virus HIV-1, conditions caused by the virus CMV, and conditions caused by fungi, e.g. *Candida* species such as *Candida albicans* and *Candida krusei, Aspergillus* and *Cryptococcus neoformans*. This listing is in no way limiting the scope of the invention.

The peptides, medicinal products, medical device and methods according to the invention are also well suited for preventive medical care by reducing the risk of developing inflammatory or infectious diseases in patients with an increased risk of attracting such complications.

The peptides of the present invention are suited for anti-inflammatory and immunomodulatory therapies, exemplified but not limited to:

1) Generally, treatment of inflammation and/or medical condition resulting from inflammation, and specifically, 2a) Intestine; Morbus Crohn, Colitis, Ulcerative colitis, 2b) Joints; Rheumatoid arthritis, Arthritis, Arthrosis, Localized disorders of muscles including muscle spasm, muscle tear, muscle injury, muscle strain, muscle sprain, 2c) Dermatology; Psoriasis, Eczema (excema), Dermatitis, Acne, 2d) Heart; Pericarditis, Endocarditis Cardiac insufficiency, 2e) Pain; (further specified under 2f below), 2f) Nervous system; Alzheimer, Multiple Sclerosis, Carpal tunnel syndrome, Disc herniation, Cervical rhizopathy, Bells palsy, Acute spinal cord injury, Spinal cord compression, Spinal stenosis, Postherpetic neuralgia, Viral encephalitis, Viral meningitis, Menieres disease, Polio and postpolio complications, Chronic Inflammatory Demyelinating Polyneuropathy, Polyneuropathy, Trigminal neuralgia, Chronic epileptic disorders, 2g) Sensory organs; Glaucoma, 2h) Mucosal surfaces (inflammation as a result of chemo/radiation therapy), 2i) Allergy, 2j) Autoimmune diseases.

The peptides of the invention are further suited for prevention and treatment of wounds and scars in connection with conditions and procedure, exemplified but not limited to:

3a) surgical procedures on various tissues such as skin, muscles, tendons, nervous tissue, blood vessels, and at different locations of the body such as eyes, ears, vocal cord, hand, spinal cord, intra-abdominal cavity, intra-thoracic cavity, intra-cranial cavity, oral cavity, gynecological procedures, endometrios, phimosis, 3b) acne.

3c) hypertrophic scars & keloids, 3d) pleuritis, 3e) peritoneal dialysis, 3f) acute and chronic wounds.

The peptides of the invention are further believed to have anti-angiogenetic effects and are therefore suited for treatment of:

4a) Cancer,

4b) Rheumatoid arthritis.

The peptides of the invention have anti-infectious effects, and are suited for the prevention and treatment of:

5a) Antibacterial effects:

Upper and lower respiratory tract (tonsillitis, sinusitis, pneumonia, chronic obstructive pulmonary disease, cystic fibrosis, etc.)

Infections of the eye (e.g. conjunctivitis)

Urinary tract infections

Sexually transmitted diseases (including antimicrobial coating of condomes)

Genital tract (including vaginosis, vaginitis, cervicitis, endometritis, PID)

Gastrointestinal tract infections (systemic infections initiated in the GI)

Central nervous system infections

Infections of the skin and skin structures such as secondarily infected traumatic lesions including surgical site infections, cellulitis or abscesses, secondarily infected dermatoses, impetigo, and carbuncles or furunculosis (including both Gram postivie and Gram negative bacteria, staphylococci, for instance MRSA, streptococci, nosocomial, wounds, burns), muscle, joints (e.g. septic arthritis), bone and hemopoietic system Infections related to the mouth, eye, inner and outer ear and ear canal, including parodontitis, gingivitis 5b) Antiviral effects:

Upper and lower respiratory tract

Sexually transmitted diseases

Gastrointestinal tract infections (systemic infections initiated in the GI)

Central nervous system infections

5c) Antifungal effects:

Upper and lower respiratory tract (such as aphthae, mucocutanous candidiasis)

Genitourinary tract (such as vulvovaginal candidiasis, balanitis)

Gastrointestinal tract infections (systemic infections initiated in the GI)

Central nervous system infections

Infections of the skin and skin structure (such as mucocutanous candidiasis), dermatosis and eczema.

Most preferably the peptides of the present invention are used for the treatment, prophylaxis and/or prevention of impetigo, burn wounds, infected abrasions, infected lacerations, excoriations, erysipelas, cellulitis, abscesses, furuncles, carbuncles, sutured wounds, surgical site infections, secondarily infected dermatoses: atopic dermatitis, psoriasis, and allergic contact dermatitis, animal bites, catheter related infection.

The peptides, medicinal products, medical device and methods according to the invention may either be used alone, in combination with each other or in combination with conventional therapy.

According to the present invention it is also possible to include the peptides, in an effective amount, in any kind of food or beverage intended to reduce infections and/or inflammations in patients running an increased risk of such conditions due to an underlying disease, a low birth weight or a medical treatment. For example, it is possible to include the peptides, in an effective amount, in an infant formula food intended to inhibit harmful effects of bacteria, such as weight loss caused by inflammation induced by bacteria, viruses or fungi in infants. When the peptides according to the invention is to be used in food stuffs, e.g. for nutritional purposes, it is especially preferred to use peptides of natural origin.

Since the peptides according to the invention have antimicrobial effects they can also be used as preservatives in different food stuffs and medicinal products such as gels, creams, ointments, pastes, solutions, emulsions etc.

The invention will now be further explained in the following examples. These examples are only intended to illustrate the invention and should in no way be considered to limit the scope of the invention.

EXAMPLES

Example 1

Peptide Screen 1

Two classes of lactoferrin derived peptides have been designed and tested. Active peptides have been identified in all classes.

Figure 1:
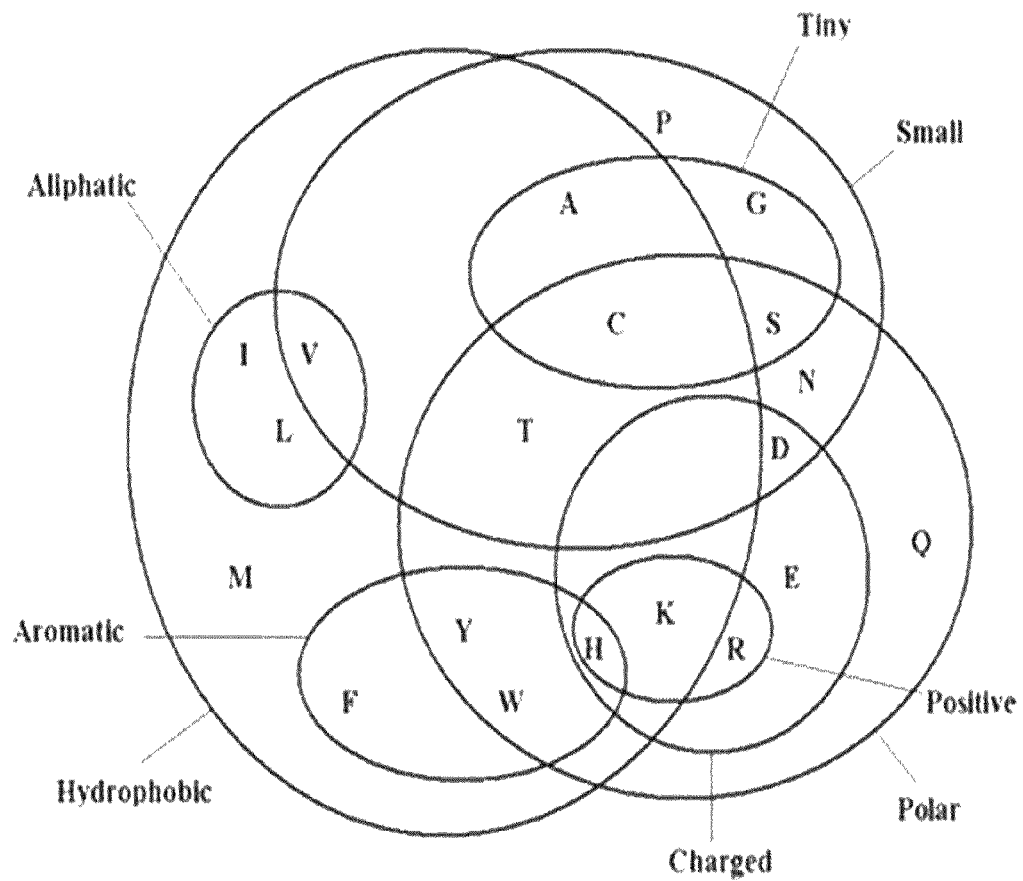
FIG. 1. Representation of the different classes of amino acids, showing similarity in terms of hydrophobicity, size and charge.
Figure 2:
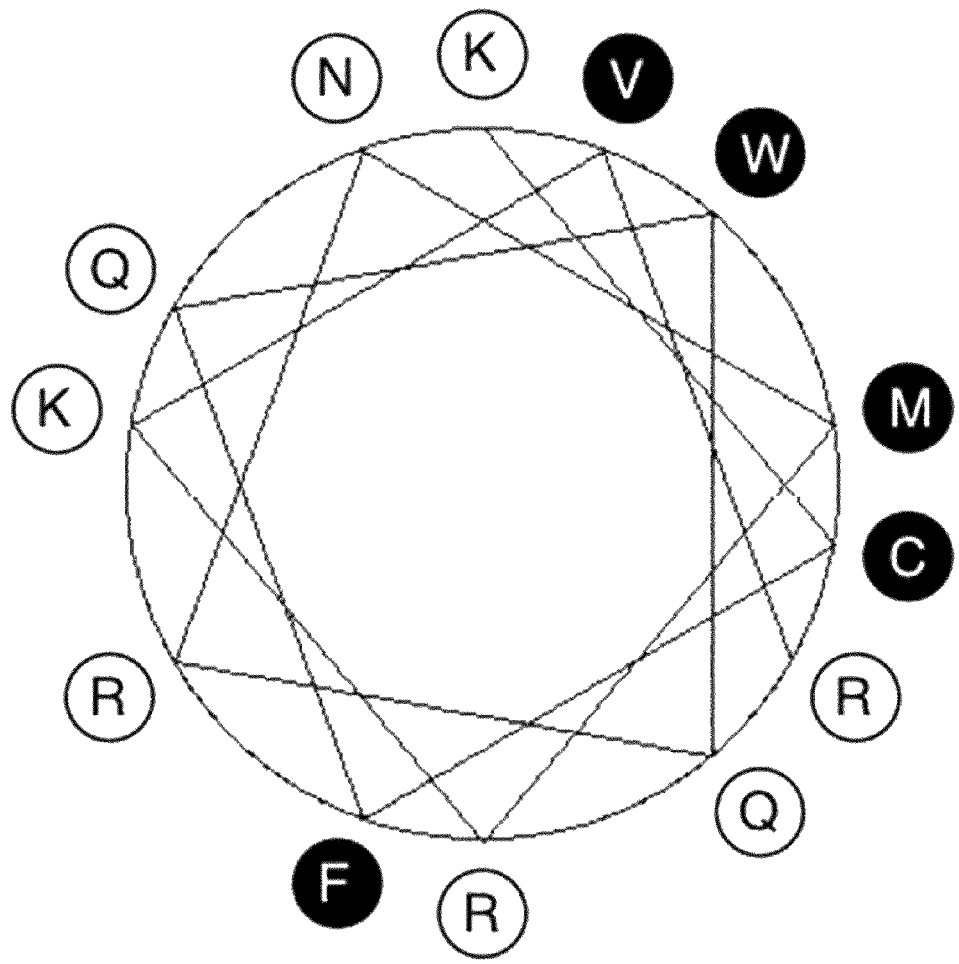
FIG. 2. Top view of the helix corresponding to a part of peptide SEQ ID NO:1, namely KCFQWQRNMRKVR (SEQ ID NO:97).

New peptide variants were designed based on the measured anti-inflammatory and antimicrobial activity of peptides having sequences similar to SEQ ID NO:1. In addition, structural considerations of the corresponding sequences for these peptides were taken into account. In practice, this meant to keep and enhance the helicity of the peptides. For the first screening round, new variants of class 1 peptides were designed by introducing N-capping motifs and (i, i+3) and (i, i+4) leucine spacing, both suggested to improve helix stability. Furthermore, the amphipathic character of the helices were modified by insertion of polar positive charged amino acids at specific positions. New variants of peptides from class 2 designed by increasing the positive charge and the hydrophobic regions of the peptides. Thus, the amphipathic character of the peptides was increased (FIG. 2). Based on the new designs, about 50 peptides were ordered as a PEPscreen library (Sigma) and tested both for anti-inflammatory and for antimicrobial activity.

TABLE 1

List of peptides tested in screen 1

| Peptide | Sequence | SEQ ID NO |
|---|---|---|
| Peptide 101 | SQPEATKCFQWQRNMRKVR | SEQ ID NO: 6 |
| Peptide 102 | NQPTATKCFQWQRNMRKVR | SEQ ID NO: 7 |
| Peptide 103 | TQPDATKCFQWQRNMRKVR | SEQ ID NO: 8 |
| Peptide 104 | QPEATKCFQWQRNMRKVR | SEQ ID NO: 9 |
| Peptide 105 | QTEADKCFQWQRNMRKVR | SEQ ID NO: 10 |
| Peptide 106 | QTEADKCFQWQRNMRKVR | SEQ ID NO: 11 |
| Peptide 107 | QSEAEKCFQWQRNMRKVR | SEQ ID NO: 12 |
| Peptide 108 | PEATKCFQWQRNMRKVR | SEQ ID NO: 13 |
| Peptide 109 | NEADKCFQWQRNMRKVR | SEQ ID NO: 14 |
| Peptide 110 | SEAEKCFQWQRNMRKVR | SEQ ID NO: 15 |
| Peptide 111 | QSLATKCFQWQRNMRKVR | SEQ ID NO: 16 |
| Peptide 112 | QSEATKLFQWQRNMRKVR | SEQ ID NO: 17 |
| Peptide 113 | QSEATKCFQWLRNMRKVR | SEQ ID NO: 18 |
| Peptide 114 | QSLATKLFQWLRNLRKVR | SEQ ID NO: 19 |
| Peptide 115 | QSEATKLFQWQRNLRKVR | SEQ ID NO: 20 |
| Peptide 117 | QSLAEKLFQWLRNLRKVR | SEQ ID NO: 21 |

TABLE 1-continued

List of peptides tested in screen 1

| Peptide | Sequence | SEQ ID NO |
|---|---|---|
| Peptide 118 | QPEATKCFPWQRNMRKVR | SEQ ID NO: 22 |
| Peptide 119 | QSEATKRFQWLRNLRKVL | SEQ ID NO: 23 |
| Peptide 120 | QSLAEKLFQWLRNRRKVR | SEQ ID NO: 24 |
| Peptide 121 | QSLATKLFQWRRNLRKVR | SEQ ID NO: 25 |
| Peptide 122 | FQWKRAMRKVR | SEQ ID NO: 26 |
| Peptide 123 | CFQWKRAMRKVR | SEQ ID NO: 27 |
| Peptide 124 | FQWQRRIRKVR | SEQ ID NO: 28 |
| Peptide 125 | FQWRRAIRKVR | SEQ ID NO: 29 |
| Peptide 128 | WFQWQRNMRKVR | SEQ ID NO: 30 |
| Peptide 129 | WFQWKRRMRKVR | SEQ ID NO: 31 |
| Peptide 131 | FWWQRKMRKVR | SEQ ID NO: 32 |
| Peptide 133 | FQWQRNMRKVR | SEQ ID NO: 33 |
| Peptide 134 | FQWQRNIRKIR | SEQ ID NO: 34 |
| Peptide 135 | FQWQRNLRKLR | SEQ ID NO: 35 |
| Peptide 136 | FQWQRNIRKVR | SEQ ID NO: 36 |
| Peptide 137 | FQWQRPIRKVR | SEQ ID NO: 37 |
| Peptide 138 | FQWQPRIRKVR | SEQ ID NO: 38 |
| Peptide 139 | FQWRPGIRKLR | SEQ ID NO: 39 |
| Peptide 140 | FQWKPAIRKVR | SEQ ID NO: 40 |
| Peptide 141 | CLNFKRGVRKIR | SEQ ID NO: 41 |
| Peptide 143 | CFQWQRKMRKVR | SEQ ID NO: 42 |
| Peptide 144 | CFQWKRAMRKVR | SEQ ID NO: 43 |
| Peptide 147 | CFKWKRKMRKVR | SEQ ID NO: 44 |
| Peptide 148 | CFQWQKRMRKVK | SEQ ID NO: 45 |
| Peptide 149 | CFQWQRNMRKVR | SEQ ID NO: 46 |
| Peptide 158 | EATKCFQWQRNMRKVR | SEQ ID NO: 47 |

Anti-Inflammatory Activity was Measured as Inhibition of TNF-α Production in LPS Stimulated THP-1 Cells.

The THP-1 cell line (TIB-202; ATCC, Manassas, Va., USA) corresponding to human monocytes was maintained in RPMI 1640 (PAA Laboratories GmbH, Pasching, Austria) supplemented with 10% fetal bovine serum (FBS; PAA Laboratories GmbH, Pasching, Austria), 1 mM sodium pyruvate (Sigma-Aldrich, St. Louis, Mo., USA), and 20 mM HEPES (PAA, Laboratories GmbH, Pasching, Austria).

The cell density was adjusted to 10$^6$ cells/ml and 100 µl of the suspension was added per well to 96-well cell culture plates (Sarstedt, Nümbrecht, Germany). The cells were treated with 10 ng/ml PMA (phorbol 12-myristate 13-acetate; Sigma-Aldrich, St. Louis, Mo., USA) for 48 hours in order to differentiate the monocytes into macrophage-like cells. Thereafter, the cells were stimulated by addition of 0.1 ng/ml lipopolysaccharide (LPS; *E. coli* serotype O55:B5; Sigma-Aldrich, St. Louis, Mo., USA) into the medium specified above except of containing 5% heat inactivated FBS. 30 minutes after addition of LPS, peptides (40 μM) were added in triplicates. After 6 hours of incubation at +37° C., 5% $CO_2$ and in a humid atmosphere, the cell supernatants were collected, centrifuged and kept frozen in −20° C. until analyzed for TNF-α content by ELISA (R&D Systems, Minneapolis, Minn., USA). The results are presented as mean relative secretion (%), with stimulated TNF-α level without peptide added set to 100% and basal secretion set to 0% (Table 2).

TABLE 2

Anti-inflammatory effects of peptides tested in screen 1

| SEQ ID NO | Peptide | TNF-α at 40 μM peptide | Class |
|---|---|---|---|
| SEQ ID NO 23 | 119 | 10% | 1 |
| SEQ ID NO 21 | 117 | 13% | 1 |
| SEQ ID NO 19 | 114 | 15% | 1 |
| SEQ ID NO 18 | 113 | 22% | 1 |
| SEQ ID NO 25 | 121 | 35% | 1 |
| SEQ ID NO 14 | 109 | 47% | 1 |
| SEQ ID NO 24 | 120 | 49% | 1 |
| SEQ ID NO 32 | 131 | 87% | 2 |
| SEQ ID NO 10 | 105 | 87% | 1 |
| SEQ ID NO 31 | 129 | 91% | 2 |
| SEQ ID NO 47 | 158 | 91% | 2 |
| SEQ ID NO 11 | 106 | 96% | 1 |
| SEQ ID NO 36 | 136 | 96% | 2 |
| SEQ ID NO 17 | 112 | 101% | 1 |
| SEQ ID NO 15 | 110 | 102% | 1 |
| SEQ ID NO 35 | 135 | 103% | 2 |
| SEQ ID NO 30 | 128 | 104% | 2 |
| SEQ ID NO 12 | 107 | 108% | 1 |
| SEQ ID NO 6 | 102 | 108% | 1 |
| SEQ ID NO 34 | 134 | 109% | 2 |
| SEQ ID NO 46 | 149 | 109% | 2 |
| SEQ ID NO 41 | 141 | 109% | 2 |
| SEQ ID NO 44 | 147 | 111% | 2 |
| SEQ ID NO 22 | 118 | 113% | 1 |
| SEQ ID NO 6 | 101 | 116% | 1 |
| SEQ ID NO 40 | 140 | 117% | 2 |
| SEQ ID NO 20 | 115 | 119% | 1 |
| SEQ ID NO 16 | 111 | 121% | 1 |
| SEQ ID NO 13 | 108 | 127% | 1 |
| SEQ ID NO 28 | 124 | 128% | 2 |
| SEQ ID NO 9 | 104 | 132% | 1 |
| SEQ ID NO 45 | 148 | 132% | 2 |
| SEQ ID NO 33 | 133 | 135% | 2 |
| SEQ ID NO 8 | 103 | 135% | 1 |
| SEQ ID NO 37 | 137 | 137% | 2 |
| SEQ ID NO 43 | 144 | 140% | 2 |
| SEQ ID NO 39 | 139 | 148% | 2 |
| SEQ ID NO 29 | 125 | 150% | 2 |
| SEQ ID NO 42 | 143 | 153% | 2 |
| SEQ ID NO 27 | 123 | 156% | 2 |
| SEQ ID NO 38 | 138 | 172% | 2 |

Antimicrobial Activity was Measured as Bactericidal Effect on *S. aureus* Using Minimal Microbicidal Concentration, $MMC_{99}$, Assay)

*S. aureus* (#1800; CCUG, Gothenburg, Sweden) cultured on blood-agar plates [Columbia agar (Oxoid, Basingstoke, UK) supplemented with 5% defibrinated horse blood (National Veterinary Institute (SVA), Uppsala, Sweden)] were transferred to brain heart infusion broth (3.7% BHI; Difco, BD Diagnostics, Franklin Lakes, N.J., USA) and incubated in a shaker at 250 rpm+37° C. over night. The culture was thereafter be diluted 1:10 in fresh BHI broth and incubated for additional two hours to reach log-phase growth. The bacteria were pelleted and suspended in 1% BHI medium (BHI broth diluted 100 times in ultra-pure water) to a concentration of $10^7$ bacteria/ml as estimated by measuring optical density at 600 nm. Peptides were serially diluted by two-fold steps from 160 μM to 1.25 μM in 1% BHI medium. The peptides (100 μl) were thereafter incubated with bacteria (5 μl á $10^7$ bact./ml) for 2 hours at +37° C. Drops (5 μl) of the suspension were placed on blood agar plates. The blood agar plates were incubated over night at +37° C. The $MMC_{99}$ values, i.e. the lowest peptide concentration needed to achieve a 99% reduction of viable bacteria, were recorded (Table 3). The concentration of the bacterial suspension used in the assay was confirmed by viable counts on blood agar plates.

TABLE 3

Antibacterial effects of peptides tested in screen 1

| SEQ ID NO | Peptide | $MMC_{99}$ μM in 1% BHI medium | Class |
|---|---|---|---|
| SEQ ID NO 19 | 114 | 2.5 | 1 |
| SEQ ID NO 21 | 117 | 2.5 | 1 |
| SEQ ID NO 32 | 131 | 5 | 2 |
| SEQ ID NO 24 | 120 | 10 | 1 |
| SEQ ID NO 25 | 121 | 10 | 1 |
| SEQ ID NO 31 | 129 | 10 | 2 |
| SEQ ID NO 43 | 144 | 10 | 2 |
| SEQ ID NO 44 | 147 | 10 | 2 |
| SEQ ID NO 46 | 149 | 13.3 | 2 |
| SEQ ID NO 16 | 111 | 20 | 1 |
| SEQ ID NO 23 | 119 | 20 | 1 |
| SEQ ID NO 26 | 122 | 20 | 2 |
| SEQ ID NO 27 | 123 | 20 | 2 |
| SEQ ID NO 28 | 124 | 20 | 2 |
| SEQ ID NO 29 | 125 | 20 | 2 |
| SEQ ID NO 30 | 128 | 20 | 2 |
| SEQ ID NO 35 | 135 | 20 | 2 |
| SEQ ID NO 41 | 141 | 20 | 2 |
| SEQ ID NO 42 | 143 | 20 | 2 |
| SEQ ID NO 45 | 148 | 20 | 2 |
| SEQ ID NO 34 | 134 | 40 | 2 |
| SEQ ID NO 39 | 139 | 45 | 2 |
| SEQ ID NO 11 | 106 | 160 | 1 |
| SEQ ID NO 14 | 109 | 160 | 1 |
| SEQ ID NO 6 | 101 | >160 | 1 |
| SEQ ID NO 7 | 102 | >160 | 1 |
| SEQ ID NO 8 | 103 | >160 | 1 |
| SEQ ID NO 9 | 104 | >160 | 1 |
| SEQ ID NO 10 | 105 | >160 | 1 |
| SEQ ID NO 12 | 107 | >160 | 1 |
| SEQ ID NO 13 | 108 | >160 | 1 |
| SEQ ID NO 15 | 110 | >160 | 1 |
| SEQ ID NO 17 | 112 | >160 | 1 |
| SEQ ID NO 18 | 113 | >160 | 1 |
| SEQ ID NO 20 | 115 | >160 | 1 |
| SEQ ID NO 22 | 118 | >160 | 1 |
| SEQ ID NO 33 | 133 | >160 | 2 |
| SEQ ID NO 36 | 136 | >160 | 2 |
| SEQ ID NO 37 | 137 | >160 | 2 |
| SEQ ID NO 38 | 138 | >160 | 2 |
| SEQ ID NO 40 | 140 | >160 | 2 |

Example 2

Peptide Screen 2

The TNF-α activities for the peptides from this first screening round were subjected to multivariate analysis using the ProPHECY™ software (Saromics, Lund, Sweden). A large number of descriptors were computed for each peptide. The TNF-α activities were then correlated with these descriptors. Separate regression models were created for each of the peptide classes. In addition, global models that considered all peptide classes were also created. Analysis of the regression model suggested several variables that contributed towards improved TNF-α activity. New peptides for the second screening round were suggested for each peptide class, primarily based on modulation of charge, amphipathicity, and hydrophobicity. Based on the new designs, about 80 peptides were ordered as a PEPscreen library (Sigma) and tested both for anti-inflammatory and antimicrobial activity.

TABLE 4

List of peptides tested in screen 2

| Peptide 201 | QREARKRFQWLRNMTKVR | SEQ ID NO: 48 |
|---|---|---|
| Peptide 202 | QESARKQFRWLRNLTKVL | SEQ ID NO: 49 |
| Peptide 203 | QREARKFRQWLRNMTKVR | SEQ ID NO: 50 |
| Peptide 204 | QSEYTKRYQWLRNLRKVL | SEQ ID NO: 51 |
| Peptide 205 | QKRATKRFQWLRNLRKVL | SEQ ID NO: 52 |
| Peptide 206 | QSERKKRFQWLRNLRKVL | SEQ ID NO: 53 |
| Peptide 207 | QSRATKRFQWHRNARKVL | SEQ ID NO: 54 |
| Peptide 208 | QSRATKRFQWLRNHRKVL | SEQ ID NO: 55 |
| Peptide 209 | QSLARTFKQWARNLRKVL | SEQ ID NO: 56 |
| Peptide 210 | QSAARTFKQWARNLRKTL | SEQ ID NO: 57 |
| Peptide 211 | QSEATKRFQWLRNLRKVLKR | SEQ ID NO: 58 |
| Peptide 212 | QSEATKRFQWLRNLRKVLWW | SEQ ID NO: 59 |
| Peptide 213 | QSEATKRFQWLRNLRKVLGP | SEQ ID NO: 60 |
| Peptide 214 | VSQSEATKRFQWLRNLRKVL | SEQ ID NO: 61 |
| Peptide 215 | KRQSLARTFKQWARNLRKVL | SEQ ID NO: 62 |
| Peptide 216 | LVKRLNRLWQFRKTAESQ | SEQ ID NO: 63 |
| Peptide 217 | QSEATKRFQWLRNLRKVL | SEQ ID NO: 64 |
| Peptide 218 | QSLAHSLFQWLRNLRKVR | SEQ ID NO: 65 |
| Peptide 219 | RSLAQKLFQWLRNLRKVR | SEQ ID NO: 66 |
| Peptide 220 | QSLARKLFQWLRNLRKVA | SEQ ID NO: 67 |
| Peptide 221 | QSLAEKLFWQLRNLRKVR | SEQ ID NO: 68 |
| Peptide 222 | NSLFEKLAQWLRQLRKVR | SEQ ID NO: 69 |
| Peptide 223 | GRRRSVQWCA | SEQ ID NO: 70 |
| Peptide 225 | QSEATKCFLWRRNMRKVR | SEQ ID NO: 71 |
| Peptide 226 | QSAKTACFLWRRNMRKVR | SEQ ID NO: 72 |
| Peptide 227 | CFLWRRNMRKVR | SEQ ID NO: 73 |
| Peptide 228 | CFLWRRLMRKLR | SEQ ID NO: 74 |
| Peptide 229 | CRLWRRNMRKVR | SEQ ID NO: 75 |
| Peptide 230 | CWLWRRAMRKVW | SEQ ID NO: 76 |
| Peptide 231 | LRLWRRLMRKVW | SEQ ID NO: 77 |
| Peptide 232 | RRLWRRWMRKVL | SEQ ID NO: 78 |
| Peptide 233 | CRLWRRRMRKVW | SEQ ID NO: 79 |
| Peptide 234 | LRTWRRLTRKVW | SEQ ID NO: 80 |
| Peptide 235 | LRLWRRSMRKVW | SEQ ID NO: 81 |
| Peptide 236 | CFLWRRSMRRLR | SEQ ID NO: 82 |
| Peptide 237 | CFLWRRLMRKV | SEQ ID NO: 83 |
| Peptide 238 | RLWRRLMRKVR | SEQ ID NO: 84 |

TABLE 4-continued

List of peptides tested in screen 2

| Peptide 239 | RWCKLWRRLMRKVRRL | SEQ ID NO: 85 |
|---|---|---|
| Peptide 240 | RWCFLWRRLMRKHRRL | SEQ ID NO: 86 |
| Peptide 241 | WCKLWRRLMRKVRR | SEQ ID NO: 87 |
| Peptide 242 | TKCFLWRRNMRKVRG | SEQ ID NO: 88 |
| Peptide 243 | WFKCFQWQRNMRKVR | SEQ ID NO: 89 |
| Peptide 244 | KKLWRRWWRKVL | SEQ ID NO: 90 |
| Peptide 245 | VWIVKKQVKRIK | SEQ ID NO: 91 |
| Peptide 246 | LVWIKRHIKKFK | SEQ ID NO: 92 |
| Peptide 247 | WRRWLRKSVKRL | SEQ ID NO: 93 |
| Peptide 248 | WCRWLRKMVKAL | SEQ ID NO: 94 |
| Peptide 249 | WRRWLRKMVKRL | SEQ ID NO: 95 |
| Peptide 255 | GRRRSVQWCA | SEQ ID NO: 96 |

Anti-Inflammatory Activity was Measured as Inhibition of TNF-α Production in LPS Stimulated THP-1 Cells.

The THP-1 cell line (TIB-202; ATCC, Manassas, Va., USA) corresponding to human monocytes was maintained in RPMI 1640 (PAA Laboratories GmbH, Pasching, Austria) supplemented with 10% fetal bovine serum (FBS; PAA Laboratories GmbH, Pasching, Austria), 1 mM sodium pyruvate (Sigma-Aldrich, St. Louis, Mo., USA), and 20 mM HEPES (PAA, Laboratories GmbH, Pasching, Austria).

The cell density was adjusted to $10^6$ cells/ml and 100 µl of the suspension was added per well to 96-well cell culture plates (Sarstedt, Nümbrecht, Germany). The cells were treated with 10 ng/ml PMA (phorbol 12-myristate 13-acetate; Sigma-Aldrich, St. Louis, Mo., USA) for 48 hours in order to differentiate the monocytes into macrophage-like cells. Thereafter, the cells were stimulated by addition of 0.1 ng/ml lipopolysaccharide (LPS; E. coli serotype O55:B5; Sigma-Aldrich, St. Louis, Mo., USA) into the medium specified above except of containing 5% heat inactivated FBS. 30 minutes after addition of LPS, peptides (40 µM, 10 µM and 4 µM) were added in triplicates. After 6 hours of incubation, the cell supernatants were collected, centrifuged, and kept frozen in −20° C. until analyzed for TNF-α content by ELISA (R&D Systems, Minneapolis, Minn., USA). The results are presented as mean relative secretion (%), with stimulated TNF-α level without peptide added set to 100% and basal secretion set to 0% (Table 5).

TABLE 5

Anti-inflammatory effects of peptides tested in screen 2

| SEQ ID NO | Peptide | TNF-α at 40 µM peptide | TNF-α at 10 µM peptide | TNF-α at 4 µM peptide | Class |
|---|---|---|---|---|---|
| 48 | 201 | 128.6% | nd | nd | 1 |
| 49 | 202 | 90.3% | nd | nd | 1 |
| 50 | 203 | 98.1% | nd | nd | 1 |
| 51 | 204 | 96.9% | nd | nd | 1 |
| 52 | 205 | 28.3% | 89.5% | 91.5% | 1 |
| 53 | 206 | 51.0% | 92.9% | 96.9% | 1 |
| 54 | 207 | 160.9% | nd | nd | 1 |
| 55 | 208 | 130.2% | nd | nd | 1 |
| 56 | 209 | 23.6% | 68.2% | 88.0% | 1 |
| 57 | 210 | 101.0% | nd | nd | 1 |

TABLE 5-continued

Anti-inflammatory effects of peptides tested in screen 2

| SEQ ID NO | Peptide | TNF-α at 40 μM peptide | TNF-α at 10 μM peptide | TNF-α at 4 μM peptide | Class |
|---|---|---|---|---|---|
| 58 | 211 | 62.8% | 89.8% | 100.7% | 1 |
| 59 | 212 | 25.7% | 85.8% | 90.9% | 1 |
| 60 | 213 | 84.4% | 125.5% | 110.3% | 1 |
| 61 | 214 | 88.8% | nd | nd | 1 |
| 62 | 215 | 1.3% | 69.6% | 86.6% | 1 |
| 63 | 216 | 121.9% | nd | nd | 1 |
| 64 | 217 | 103.0% | nd | nd | 1 |
| 65 | 218 | 9.2% | 55.7% | 81.8% | 1 |
| 66 | 219 | 7.3% | 44.0% | 68.5% | 1 |
| 67 | 220 | 11.6% | 37.0% | 70.8% | 1 |
| 68 | 221 | 94.4% | nd | nd | 1 |
| 69 | 222 | 32.9% | 65.9% | 89.2% | 1 |
| 70 | 223 | 104.4% | nd | nd | other |
| 71 | 225 | 111.6% | nd | nd | 1 and 2 |
| 72 | 226 | 108.7% | nd | nd | 1 and 2 |
| 73 | 227 | 111.0% | nd | nd | 2 |
| 74 | 228 | 53.6% | 95.4% | 106.6% | 2 |
| 75 | 229 | 108.5% | nd | nd | 2 |
| 76 | 230 | 80.4% | 135.6% | 119.2% | 2 |
| 77 | 231 | 49.8% | 89.1% | 102.6% | 2 |
| 78 | 232 | 33.2% | 66.6% | 96.9% | 2 |
| 79 | 233 | 90.7% | nd | nd | 2 |
| 80 | 234 | 102.0% | nd | nd | 2 |
| 81 | 235 | 89.3% | nd | nd | 2 |
| 82 | 236 | 94.4% | nd | nd | 2 |
| 83 | 237 | 89.2% | nd | nd | 2 |
| 84 | 238 | 76.5% | 89.2% | 83.9% | 2 |
| 85 | 239 | 7.4% | 56.5% | 65.6% | 2 |
| 86 | 240 | 40.1% | 59.9% | 78.3% | 2 |
| 87 | 241 | 8.1% | 57.9% | 92.7% | 2 |
| 88 | 242 | 116.8% | nd | nd | 2 |
| 89 | 243 | 113.1% | nd | nd | 2 |
| 90 | 244 | 10.7% | 116.7% | 107.7% | 2 |
| 91 | 245 | 146.3% | nd | nd | 2 |
| 92 | 246 | 125.5% | nd | nd | 2 |
| 93 | 247 | 88.2% | nd | nd | 2 |
| 94 | 248 | 24.2% | 80.2% | 87.1% | 2 |
| 95 | 249 | −0.7% | 78.0% | 91.2% | 2 |
| 96 | 255 | 100.7% | nd | nd | other | nd = not done

Antimicrobial Activity was Measured as Bactericidal Effect on *S. aureus* Using Minimal Microbicidal Concentration, $MMC_{99}$, Assay)

*S. aureus* (#1800; CCUG, Gothenburg, Sweden) cultured on blood-agar plates [Columbia agar (Oxoid, Basingstoke, UK) supplemented with 5% defibrinated horse blood (National Veterinary Institute (SVA), Uppsala, Sweden)] were transferred to brain heart infusion broth (3.7% BHI; Difco, BD Diagnostics, Franklin Lakes, N.J., USA) and incubated in a shaker at 250 rpm+37° C. over night. The culture was thereafter be diluted 1:10 in fresh BHI broth and incubated for additional two hours to reach log-phase growth. The bacteria were pelleted and suspended in 1% BHI medium (BHI broth diluted 100 times in ultra-pure water) to a final concentration of $10^7$ bacteria/ml as estimated by measuring optical density at 600 nm.

Peptides were serially diluted by two-fold steps from 400 μM to 0.78 μM in either 1% BHI medium or in 50% heat inactivated simulated wound fluid [SWF, containing 1 part 0.1% peptone (Oxoid, Basingstoke, UK) in saline and 1 part fetal bovine serum, diluted 2 times in ultra-pure water].

The peptides (100 μl) were thereafter incubated with bacteria (5 μl á $10^7$ bact./ml) for 2 hours at +37° C. Drops (5 μl) of the suspension were placed on blood agar plates. The blood agar plates were incubated over night at +37° C. The $MMC_{99}$ values, i.e. the lowest peptide concentration needed to achieve a 99% reduction of viable bacteria were recorded (Table 6). The concentration of the bacterial suspension used in the assay was confirmed by viable counts on blood agar plates.

TABLE 6

Antibacterial effects of peptides tested in screen 2

| SEQ ID NO | Peptide | $MMC_{99}$ μM in 1% BHI medium | $MMC_{99}$ μM in 50% SWF | Class |
|---|---|---|---|---|
| 52 | 205 | 12.5 | 50 | 1 |
| 53 | 206 | 12.5 | 100 | 1 |
| 56 | 209 | 12.5 | 100 | 1 |
| 58 | 211 | 6.25 | 100 | 1 |
| 59 | 212 | 12.5 | 100 | 1 |
| 60 | 213 | 25 | 200 | 1 |
| 62 | 215 | 6.25 | 25 | 1 |
| 65 | 218 | 6.25 | 50 | 1 |
| 66 | 219 | 6.25 | 12.5 | 1 |
| 67 | 220 | 12.5 | 25 | 1 |
| 69 | 222 | 12.5 | 100 | 1 |
| 70 | 223 | 25 | nd | other |
| 74 | 228 | 12.5 | 50 | 2 |
| 76 | 230 | 25 | 100 | 2 |
| 77 | 231 | 12.5 | 50 | 2 |
| 78 | 232 | 12.5 | 25 | 2 |
| 84 | 238 | 12.5 | 100 | 2 |
| 85 | 239 | 12.5 | 25 | 2 |
| 86 | 240 | 12.5 | 25 | 2 |
| 87 | 241 | 12.5 | 25 | 2 |
| 90 | 244 | 12.5 | 50 | 2 |
| 94 | 248 | 25 | 50 | 2 |
| 95 | 249 | 12.5 | 6.25 | 2 |
| 96 | 255 | 25 | nd | other | nd = not done

Class 2 Peptides

Several variants of peptides were designed with increased charge and added hydrophobic regions. Especially modulation of amphipathicity was important to achieve peptides with high activity.

Figure 3:
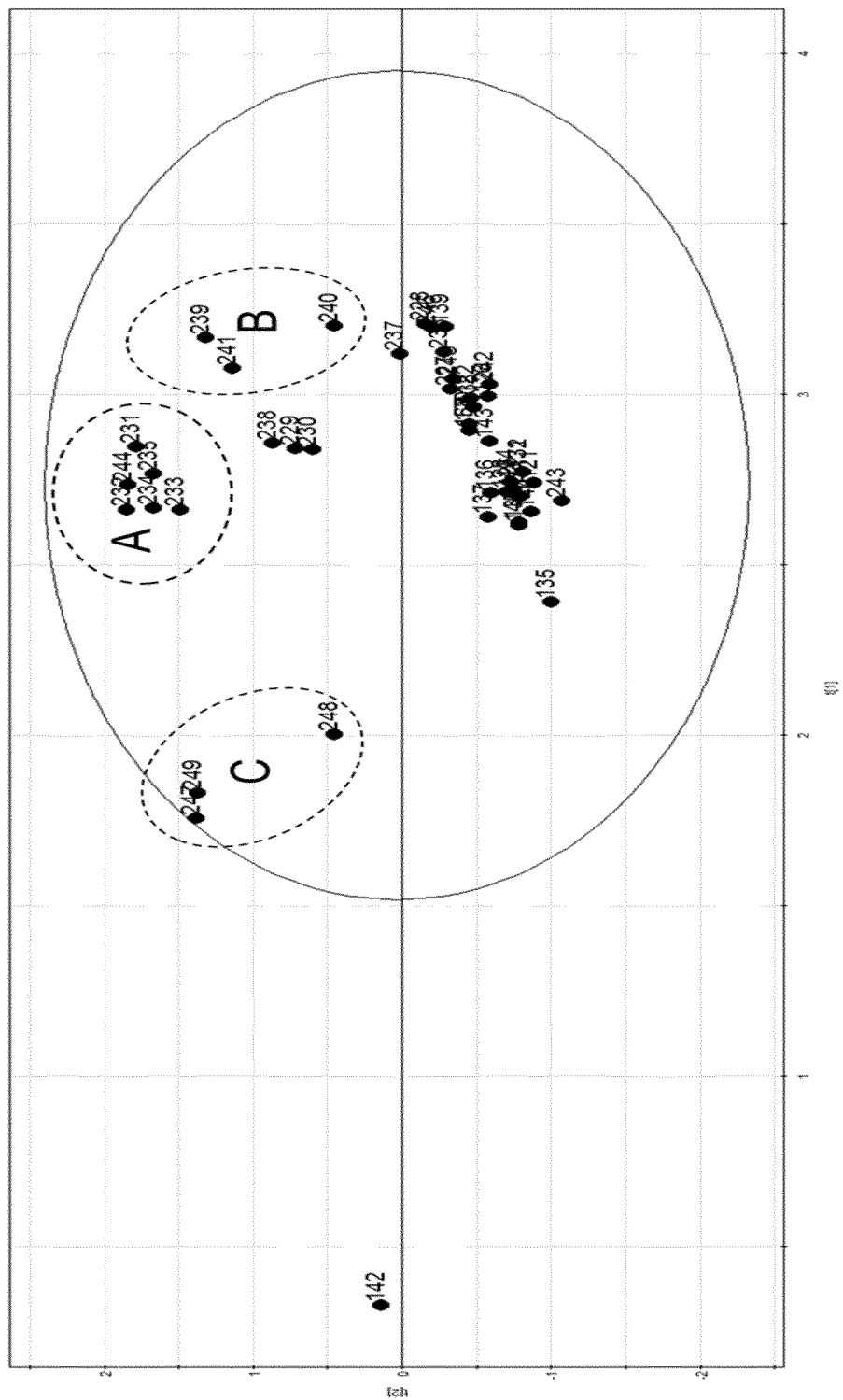
FIG. 3. Scatter plot showing clustering of class 2 peptides. Peptides are plotted according to their physicochemical properties. Peptides with TNF-α inhibitory activity (at a peptide concentration of 40 μM) can be found in three clusters: clusters A, B and C.

Based on a principal component analysis (ProPHECY™) using the class 2 peptide sequences and the results from the anti-inflammatory assay, three different clusters of active peptides were identified (FIG. 3). The clusters only contained peptides from screening round 2. The most active peptides from each cluster are summarized in Table 7.

The scatter plot in FIG. 3 is based on a principal component analysis of the peptide properties. The peptides have been aligned and the physicochemical properties of each amino acid are considered. Peptides that are close to each other in the plot are also expected to have a higher degree of similarity. That is, the peptides have the same or similar amino acids in most positions. Correspondingly distant peptides are expected to have more dissimilar sequence. For instance, peptides 232 and 244 are very close (see cluster A) and they differ at three positions where 232 have R, R and M and 244 have K, K and W (R and K, and M and W, are not very different). This can be compared with peptides 240 and 249 (cluster B and C respectively) which differ by two residues in length in addition to differences at eight positions. Hence, the score plot gives an overview of the physicochemical similarity between the peptides.

TABLE 7

Class 2 peptides

| | Position: | | | | | | | | | | | | | | | |
|---|---|---|---|---|---|---|---|---|---|---|---|---|---|---|---|---|
| | −2 | −1 | 1 | 2 | 3 | 4 | 5 | 6 | 7 | 8 | 9 | 10 | 11 | 12 | 13 | 14 |
| | | | | | | | Template: | | | | | | | | | |
| | x | x | C | F | Q | W | Q | R | N | M | R | K | V | R | x | x |
| CLUSTER A | | | | | | | | | | | | | | | | |
| 231: | | | L | R | L | | R | | L | | | | | W | | |
| 232: | | | R | R | L | | R | | W | | | | | L | | |
| 233: | | | | R | L | | R | | R | | | | | W | | |
| 235: | | | L | R | L | | R | | S | | | | | W | | |
| 244: | | | K | K | L | | R | | W | W | | | | L | | |
| CLUSTER B | | | | | | | | | | | | | | | | |
| 239: | R | W | | K | L | | R | | L | | | | | | R | L |
| 240: | R | W | | | L | | R | | L | | | | H | | R | L |
| 241: | | W | | K | L | | R | | L | | | | | R | | |
| CLUSTER C | | | | | | | | | | | | | | | | |
| 247: | | | W | R | R | | L | | K | S | V | | R | L | | |
| 248: | | | W | C | R | | L | | K | | V | | A | L | | |
| 249: | | | W | R | R | | L | | K | | V | | R | L | | |

Residues in bold indicate amino acid types that contribute positively to the activity.

The overview of the results in Table 7 makes it easier to identify positions and mutations that are important for high activity. In these peptides several positions have been replaced with positively charged amino acids such as Lys (K) and Arg (R). In addition, several positions have been changed to hydrophobic amino acids in order to increase hydrophobicity in the peptide ends and to increase and modulate the amphipathicity. ProPHECY™ analysis shows that it is beneficial to have a positively charged amino acid at positions 1 and 2 as well as in position 5. Furthermore, hydrophobic amino acids are beneficial in positions 7, 8 and 12. All these peptides have a Leu (L) in position 3. The amphipathicity is thus improved if positions 7, 8 and 12 are changed to hydrophobic residues or changed to residues with increased hydrophobicity (as Met to Trp in peptide 244).

Peptides in cluster B have been extended both in the N-terminus and the C-terminus with one or two residues in order to increase positive charge and hydrophobicity. Peptide 240 is less active due to that positive charge and amphipathicity is lower for this peptide. The most active ones peptides 239 and 241 have positively charged amino acids in positions 2 and 5 and hydrophobic amino acids in positions 3 and 7.

In the cluster C peptides the amphipathicity has been moved and "rotated" to another part of the surface along the peptide. This is achieved by replacing position 1, 5, 9 and 12 with hydrophobic amino acids and 2, 3, 7 and 11 with positively charged amino acids.

Finally, some of the active class 2 peptides belonging to cluster A and especially cluster B display high antimicrobial effects even at close to physiological salt concentrations.

Example 3

In Vitro Antimicrobial Effect

The antimicrobial effects of the peptides 232 (SEQ ID NO: 78), and 220 (SEQ ID NO:67) were analysed by $MMC_{99}$ (minimal microbicidal concentration) assay against *S. aureus* (CCUG 1800), MRSA (CCUG 41879), *P. aeruginosa* (ATCC 15442), *E. coli* (CCUG 31246), *S. pyogenes* (CCUG 4207), *P. acnes* (CCUG 1794T), *S. epidermidis* (ATCC12228), *K. pneumoniae* (ATCC 13883), *A. baumannii* (ATCC 19606), and *C. albicans* (ATCC 64549). The peptides were purchased from Biopeptide Company (San Diego, Calif., USA) and Bachem AG (Bubendorf, Switzerland) and results are presented in Table 8A and 8B respectively.

Peptides were serially diluted in two different assay medium, 1% BHI medium (brain-heart infusion medium) or 50% heat inactivated simulated wound fluid (SWF), and thereafter incubated with the microorganisms for 2 hours. Drops of the suspension were placed on blood agar plates. The $MMC_{99}$ values, i.e. the lowest peptide concentration needed to achieve a 99% reduction of viable microorganisms, were recorded. As presented in Table 8, all the peptides have the ability to kill microorganisms frequently appearing in infections.

TABLE 8A

In vitro antimicrobial effect measured as MMC99 (µg/ml)

| | Peptide 232 (SEQ ID NO 78) | | Peptide 220 (SEQ ID NO 67) | |
|---|---|---|---|---|
| | 1% BHI | 50% SWF | 1% BHI | 50% SWF |
| S. aureus | 5 | 44 | 7 | 28 |
| MRSA | 6 | 100 | 6 | 200 |
| P. aeruginosa | 5 | >176 | 7 | >200 |
| E. coli | 5 | >176 | 3 | >200 |
| P. acnes | 6 | >200 | <3 | 100 |
| S. pyogenes | <3 | >200 | <3 | 50 |

TABLE 8B

In vitro antimicrobial effect measured as MMC99 (µg/ml)

| | Peptide 232 (SEQ ID NO 78) | |
|---|---|---|
| | 1% BHI | 50% SWF |
| S. epidermidis | 3 | 50 |
| K. pneumoniae | 6 | >200 |

TABLE 8B-continued

In vitro antimicrobial effect measured as MMC99 (μg/ml)

| | Peptide 232 (SEQ ID NO 78) | |
|---|---|---|
| | 1% BHI | 50% SWF |
| A. baumannii | 3 | 200 |
| C. albicans | 3 | 50 |

Example 4

In Vivo Antimicrobial Effect in Excision Wound Model in Rats

Figure 4:
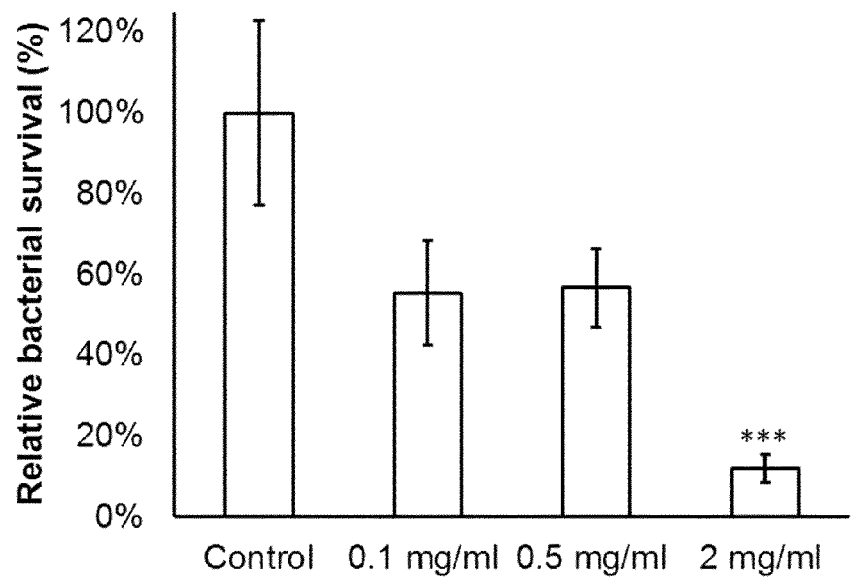
FIG. 4. Dose-response effect of peptide 232 (SEQ ID NO 78)(A) and peptide 220 (SEQ ID NO 67)(B) on bacterial colonization of infected excision wounds in rats. Wounds infected with MRSA (CCUG 41879) and treated with the corresponding peptide in $H_2O$, in the concentrations 0.1, 0.5 and 2 mg/ml, demonstrate a significant reduction in bacterial counts in a dose response fashion. Results are presented as relative bacterial survival (%) compared to control group±SEM (n=15 wounds). Statistical significance was estimated by Student's t test. *=$p<0.05$, =$p<0.01$, *=$p<0.001$.
Figure 4:
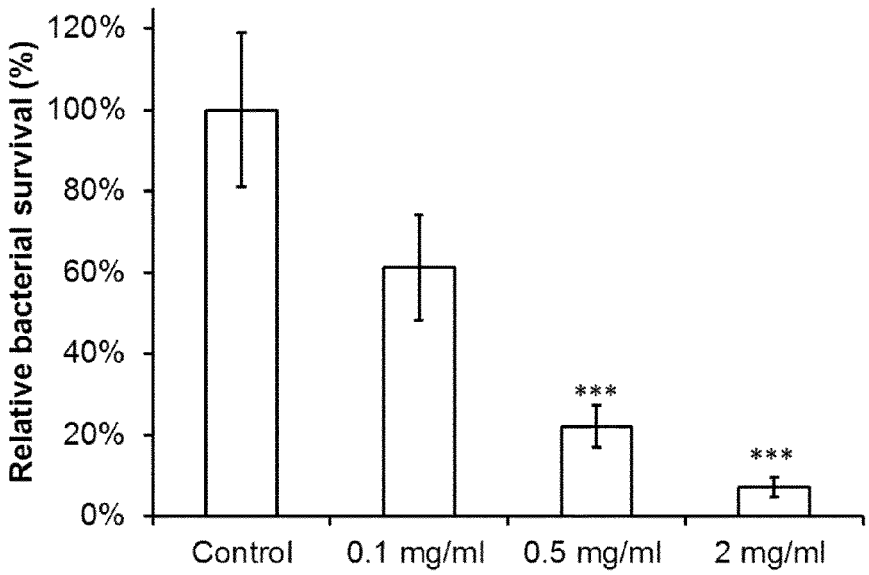

The in vivo antimicrobial effects of the peptide 232 (SEQ ID NO: 78), and the peptide 220 (SEQ ID NO:67) were investigated in an excision wound model in rats. The wounds were inoculated with methicillin resistant S. aureus (MRSA) for two hours, followed by a single administration of peptide or control ($H_2O$) for two hours before termination and harvest of the bacteria. All peptides showed pronounced antimicrobial effect (FIG. 4).

Example 5

In Vivo Antimicrobial Effect in Infected Wounds in Pig

Figure 5:
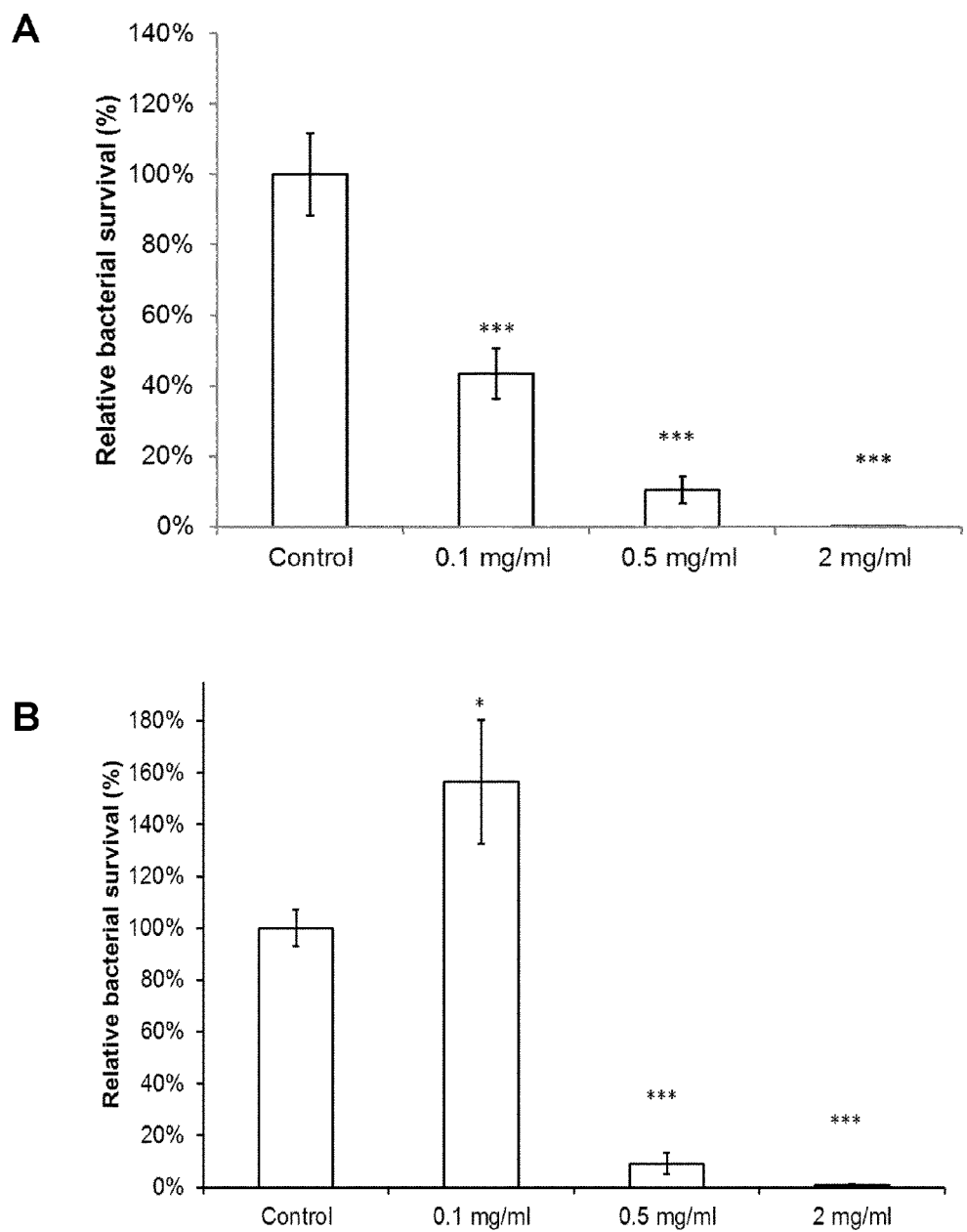
FIG. 5. Dose response effect of, peptide 232 (SEQ ID NO 78)(A) and peptide 220 (SEQ ID NO 67)(B) on bacterial colonization of infected wounds in pig skin. Wounds infected with *S. aureus* in PBS/serum (50/50) and treated with corresponding peptide in H$_2$O, in the concentrations 0.1, 0.5 and 2 mg/ml demonstrate a significant reduction in bacterial counts with a dose response relation. Results are presented as relative bacterial survival (%) compared to control group±SEM (n=10 wounds). Statistical significance was estimated by Student's t test. *=p<0.05, =p<0.01, *=p<0.001.

The antimicrobial effects of the peptide 232 (SEQ ID NO: 78), and the peptide 220 (SEQ ID NO:67) were investigated in an ex vivo model on pig skin. The wounds were inoculated with S. aureus in the presence of PBS/Serum 50/50. Two hours after inoculation the wounds were treated with a single administration of the peptide or placebo ($H_2O$). Four hours after the treatment bacteria were harvested and viable counts of each wound were determined. The results confirm the findings in rat indicating that the peptides are highly effective anti-infectious agents when applied locally (FIG. 5).

The invention claimed is:

1. An isolated peptide comprising at least an amino acid sequence selected from the group consisting of:

C-F-L-W-R-R-L-M-R-K-L-R, (SEQ ID NO: 74)

C-W-L-W-R-R-A-M-R-K-V-W, (SEQ ID NO: 76)

L-R-L-W-R-R-L-M-R-K-V-W, (SEQ ID NO: 77)

R-R-L-W-R-R-W-M-R-K-V-L, (SEQ ID NO: 78)

C-R-L-W-R-R-R-M-R-K-V-W, (SEQ ID NO: 79)

L-R-L-W-R-R-S-M-R-K-V-W, (SEQ ID NO: 81)

K-K-L-W-R-R-W-W-R-K-V-L, (SEQ ID NO: 90)

R-W-C-K-L-W-R-R-L-M-R-K-V-R-L, (SEQ ID NO: 85)

R-W-C-F-L-W-R-R-L-M-R-K-H-R-L, (SEQ ID NO: 86)

W-C-K-L-W-R-R-L-M-R-K-V-R-R, (SEQ ID NO: 87)

W-R-R-W-L-R-K-S-V-K-R-L, (SEQ ID NO: 93)

W-C-R-W-L-R-K-M-V-K-A-L, and (SEQ ID NO: 94)

W-R-R-W-L-R-K-M-V-K-R-L. (SEQ ID NO: 95)

2. The isolated peptide according to claim 1 consisting of a peptide selected from the group consisting of:

C-F-L-W-R-R-L-M-R-K-L-R, (SEQ ID NO: 74)

C-W-L-W-R-R-A-M-R-K-V-W, (SEQ ID NO: 76)

L-R-L-W-R-R-L-M-R-K-V-W, (SEQ ID NO: 77)

R-R-L-W-R-R-W-M-R-K-V-L, (SEQ ID NO: 78)

-continued

C-R-L-W-R-R-M-R-K-V-W, (SEQ ID NO: 79)

L-R-L-W-R-R-S-M-R-K-V-W, (SEQ ID NO: 81)

K-K-L-W-R-R-W-W-R-K-V-L, (SEQ ID NO: 90)

R-W-C-K-L-W-R-R-L-M-R-K-V-R-R-L, (SEQ ID NO: 85)

R-W-C-F-L-W-R-R-L-M-R-K-H-R-R-L, (SEQ ID NO: 86)

W-C-K-L-W-R-R-L-M-R-K-V-R-R (SEQ ID NO: 87)

W-R-R-W-L-R-K-S-V-K-R-L, (SEQ ID NO: 93)

W-C-R-W-L-R-K-M-V-K-A-L, and (SEQ ID NO: 94)

W-R-R-W-L-R-K-M-V-K-R-L. (SEQ ID NO: 95)

3. The isolated peptide according to claim 1, further comprising $CONH_2$ at the carboxy terminal end.

4. The isolated peptide according to claim 1, further comprising $CONH_2$ at the carboxy terminal end and $CH_3CONH$ at the amino terminal end.

5. The isolated peptide according to claim 1, further comprising $CONH_2$ at the carboxy terminal end and $CH_3CONH$ at the amino terminal end, and an acetamidomethyl-cysteine in place of a cysteine residue.

6. A pharmaceutical composition comprising a peptide according to claim 1, claim 2, claim 3, claim 4, or claim 5.

7. A method for treating bacterial and fungal infections comprising administering to a patient in need thereof an effective amount of the pharmaceutical composition according to claim 6.

8. A method for treating impetigo; infected burn wounds; infected abrasions; infected lacerations; infected excoriations; erysipelas; cellulitis; abscesses; furuncles; carbuncles; infected sutured wounds; infected surgical site infections; secondarily infected dermatoses: atopic dermatitis, psoriasis, and allergic contact dermatitis; infected animal bite wounds and catheter related infections, all of which are caused by bacterial and/or fungal infections, comprising administering to a patient in need thereof an effective amount of the pharmaceutical composition according to claim 6.

9. The method according to claim 7 or claim 8, wherein said administration is oral administration, systemic administration, parenteral administration, local administration, or topical administration.

10. A food stuff comprising a peptide according to claim 1, claim 2, claim 3, claim 4, or claim 5.

11. A medicament comprising the peptide according to claim 1, claim 2, claim 3, claim 4, or claim 5.

12. An isolated peptide consisting of the amino acid sequence R-R-L-W-R-R-W-M-R-K-V-L (SEQ ID NO:78).

* * * * *